United States Patent
Fontaine et al.

(10) Patent No.: US 8,420,679 B2
(45) Date of Patent: Apr. 16, 2013

(54) AMINOTHIAZOLE DERIVATIVES AND THEIR USE AS CRF RECEPTOR LIGANDS

(75) Inventors: Evelyne Fontaine, Escalquens (FR); Michel Geslin, Villeneuve Tolosane (FR); Danielle Gully, Saubens (FR); Antoine Pradines, Roquettes (FR); Pierre Roger, Montigny-le-Bretonneux (FR)

(73) Assignee: Sanofi, Paris (FR)

( * ) Notice: Subject to any disclaimer, the term of this patent is extended or adjusted under 35 U.S.C. 154(b) by 788 days.

(21) Appl. No.: 11/740,001

(22) Filed: Apr. 25, 2007

(65) Prior Publication Data

US 2007/0281919 A1 Dec. 6, 2007

Related U.S. Application Data

(60) Continuation of application No. 10/452,451, filed on Jun. 2, 2003, now abandoned, which is a division of application No. 10/031,038, filed as application No. PCT/FR00/01995 on Jul. 11, 2000, now Pat. No. 6,586,456.

(30) Foreign Application Priority Data

Jul. 15, 1999 (FR) ..................................... 99 09144

(51) Int. Cl.
*A61K 31/425* (2006.01)

(52) U.S. Cl.
USPC ............................ 514/366; 514/370; 548/181

(58) Field of Classification Search ................ 514/366, 514/370; 548/181, 190, 193
See application file for complete search history.

(56) References Cited

U.S. PATENT DOCUMENTS

| 5,464,847 A | 11/1995 | Courtemanche et al. |
| 5,602,132 A | 2/1997 | Roger et al. |
| 5,880,135 A | 3/1999 | Gully et al. |
| 6,344,470 B1 | 2/2002 | Fontaine et al. |

FOREIGN PATENT DOCUMENTS

| EP | 0 576 350 A1 | 12/1993 |
| EP | 0 659 747 A1 | 6/1995 |
| WO | WO 97/00868 | 1/1997 |
| WO | WO 98/15543 | 4/1998 |

OTHER PUBLICATIONS

Derwent Patent Abstract No. 199821, 1998.
International Search Report for WO2001/05776 dated Jan. 25, 2001.

*Primary Examiner* — Sreeni Padmanabhan
*Assistant Examiner* — Shobha Kantamneni
(74) *Attorney, Agent, or Firm* — Serena Farquharson-Torres; Scully, Scott, Murphy & Presser, P.C.

(57) ABSTRACT

Substituted 4-phenyl-2-aminothiazole derivatives, processes for preparing the same, and the use thereof as corticotrophin releasing factor (CRF) antagonists.

6 Claims, No Drawings

AMINOTHIAZOLE DERIVATIVES AND THEIR USE AS CRF RECEPTOR LIGANDS

The present invention relates to novel branched aminothiazole derivatives, to a process for preparing them and to pharmaceutical compositions containing them. These novel thiazole derivatives have antagonist activity towards CRF (corticotropin releasing factor) and can thus constitute active principles for pharmaceutical compositions.

Corticotropin releasing factor (CRF) is a peptide whose sequence of 41 amino acids was characterized by W. Vale et al. in 1981 (Science, 1981, 213, 1394-1397). CRF is the main endogenous factor involved in regulating the hypothalamo-hypophysoadrenal axis (release of adrenocorticotropic hormone: ACTH) and its pathologies, as well as in the depressive syndromes arising therefrom. CRF also brings about the secretion of β-endorphin, β-lipotropin and corticosterone. CRF is thus the physiological regulator of the secretion of adrenocorticotropic hormone (ACTH) and more generally of peptides derived from propiomelanocortin (POMC). Besides its location in the hypothalamus, CRF is also widely distributed in the central nervous system, as well as in extra-neuronal tissues such as the adrenal glands and the testicles. The presence of CRF has also been demonstrated in the course of inflammatory processes.

Numerous animal experiments have shown that the central administration of CRF causes various anxiogenic effects such as modification of the behaviour in general: for example neophobia, reduction in sexual receptivity, decrease in food consumption and in slow-wave sleep in rates. The intracerebroventricular injection of CRF also increases the excitation of the noradrenergic neurons of the locus coeruleus which is often associated in animals with a state of anxiety. In rates, the central or peripheral administration of CRF or of similar peptides (for example urocortine or sauvagine) induces, in addition to central effects such as heightening consciousness and emotional reactivity towards the environment, modification sin gastric drainage, in acid secretion, in intestinal transit and in faecal excretion, as well as tension effects. CRF is also involved in the complex regulation of inflammatory responses, firstly with a pro-inflammatory role in certain animal models, and secondly as an inhibitor of the effects induced by increasing the vascular permeability following inflammation.

The use of a peptide antagonist, alpha-helical CRF(9-41) (α-CRF) or of specific antibodies (Rivier J. et al., Science, 1984, 224, 889-891) confirms the role of this peptide in all of these effects. These experiments also confirmed the important role of CRF in man in the integration of the complex responses observed during a physiological, psychological or immunological stress both in neuroendocrinal and visceral as well as behavioural terms (Morley J. E. et al., Endocrine Review, 1987, 8, 3, 256-287; Smith M. A. et al., Horm. Res., 1989, 31, 66-71). In addition, clinical data argue in favour of the effective involvement of CRF in the many disorders resulting fro ma condition of stress (Gulley L. R. et al., J. Clin. Psychiatry, 1993, 54, 1, (suppl.), 16-19), for example:

the existence of the CRF test (i.v. administration) in man has made it possible to demonstrate the modification of the ACTH response in depressive patients (Breier A. et al., Am. J. Psychiatry, 1987, 144, 1419-1425), the discovery of a hypersecretion of endogenous CRF in certain pathologies, for example an elevated level of CRF in the cephalorrachidian fluid in non-medicated patients who are depressed or suffering form a dementia such as Alzheimer's disease (Nemeroff C. B. et al., Science, 1984, 226, 4680, 1342-1343; Regul. Pept., 1989, 25, 123-130), or a decreased density of CRF receptors in the cortex of suicide victims (Nemeroff C. B. et al., Arch. Gen. Psychiatry, 1988, 45, 577-579), the dysfunctioning of CRF-dependent neurons is even suggested in severe pathologies such as Alzheimer's disease, Parkinson's disease, Huntington's chorea and amyotropic lateral sclerosis (De Souza E. B., Hospital Practice, 1988, 23, 59).

The central administration of CRF in many animal species produces behavioural effects similar to those obtained in man under stress conditions. When they are repeated over time, these effects may result in various pathologies such as: fatigue, hypertension, cardiac and tension disorders, modification of gastric drainage or of faecal excretion (colitis, irritable bowel), modification of acid secretion, hyperglycaemia, retarded growth, anorexia, neophobia, migraines, reproductive disorders, immunosuppression (inflammatory processes, multiple infections and cancers) and various neuropsychiatric disorders (depression, anorexia nervosa and anxiety).

The intracerebroventricular injection of the reference peptide antagonist, α-CRF, prevents the effects obtained either by administration of exogenous CRF or by the use of stress-inducing agents (ether, restraint, noise, electric shock, ethanol withdrawal symptoms or surgery) which are capable by themselves of inducing an increase in the level of endogenous CRF. These results are confirmed by the study of many antagonist peptide molecules that are structurally similar to CRF and that have a prolonged duration of action relative to α-CRF (Rivier J. et al., J. Med. Chem., 1993, 36, 2851-2859; Menzaghi F. et al., J. Pharmacol. Exp. Ther., 1994, 269, 2, 564-572; Hernandez J. F. et al., J. Med. Chem., 1993, 36, 2860-2867).

Such CRF-antagonist peptide compounds are described, for example, in U.S. Pat. Nos. 5,109,111, 5,132,111 and 5,245,009 and in patent applications WO 92/22576 and WO 96/19499.

In addition, preliminary studies have shown that tricyclic antidepressants can modulate the level of CRF as well as the number of CRF receptors in the brain (Grigoriadis D. E. et al., Neuropsychopharmacology, 1989, 2, 53-60). Similarly, benzodiazepine anxiolytic agents are capable of reversing the effect of CRF (Britton K. T. et al., Psychopharmacology, 1988, 94, 306), although the mechanism of action of these substances has not been entirely elucidated. These results reinforce, if necessary, the growing need for non-peptide antagonist molecules for CRF receptors.

It is also important to point out three possible consequences of conditions of chronic stress, namely immunodepression, fertility disorders and the development of diabetes.

CRF exerts such effects by interacting with specific membrane receptors which have been characterized in the pituitary gland and the brain of many species (mice, rats and man) as well as in the heart, the skeletal muscle (rats and mice) and in the myometrium and the placenta during pregnancy.

A large number of 2-aminothiazole derivatives are already known. Patent application EP 462 264 describes 2-aminothiazole derivatives, in which the tertiary amine in position 2 comprises two substituents each containing at least one hetero atom including an amine derivative. These compounds are platelet activation factor antagonists (PAF-acether) and find their applications in the treatment of asthma, certain allergic or inflammatory conditions, cardiovascular diseases, hypertension and various renal pathologies, or alternatively as contraceptive agents.

Patent application GB 2 022 285 describes compounds with regulatory activity on the immune response and with anti-inflammatory properties. These are thiazole derivatives substituted in position 2 with secondary amine groups.

Certain 2-aminothiazole derivatives have been described in patent application EP 432 040. These compounds are antagonists of cholecystokinin and gastrin.

2-Amino-4,5-diphenylthiazole derivatives with anti-inflammatory properties are also known (patent application JP-01 75 475).

2-Amino-4-(4-hydroxyphenyl)thiazole derivatives which are useful as synthetic intermediates for the preparation of 2,2-diarylchromenothiazole derivatives are also known (patent application EP 205 069).

2-(N-Methyl-N-benzylamino)thiazole derivatives are also described in J. Chem. Soc. Perkin, Trans. 1, 1984, 2, 147-153 and in J. Chem. Soc. Perkin, Trans. 1, 1983, 2, 341-347.

Patent application WO 94/01423 describes 2-aminothiazole derivatives. These compounds are used as insecticides; they carry no substitution in position 5 of the heterocycle.

Similarly, patent application WO 96/1650 describes compounds derived from 2-aminothiazole. These compounds are used as antibodies.

Patent application EP 283 390 describes, among other thiazole derivatives, 2-(N-alkyl-N-pyridylalkylamino)thiazole derivatives in which the amine in position 2 is substituted with an unbranched pyridylalkyl radical.

These compounds in particular have stimulatory activity on central cholinergic transmission. They can thus be used as muscarine receptor agonists and find their application in the treatment of memory disorders and sensile dementias.

2-Aminothiazole derivatives in which the amine in position 2 is a tertiary a mine bearing a branched alkyl or aralkyl substituent have been described in EP 576 350 and in EP 659 747 as having affinity for the CRF receptors. None of these compounds carries a substituted phenyl as a substituent of the tertiary amine in position 2 of the thiazole nucleus.

U.S. Pat. No. 5,063,245 describes CRF antagonists which allow the in vitro displacement of the binding of CRF to its specific receptors at a concentration in the region of one micromole. Numerous patent applications regarding non-peptide molecules have since been published, for example patent applications WO 94/13643, WO 94/13644, WO 94/13661, WO 94/13676, WO 94/13677, WO 94/10333, WO 95/00640, WO 95/10506, WO 95/13372, WO 95/33727, WO 95/33750, WO 95/34563, EP 691 128 or EP 729 758.

It has now been found according to the present invention that certain branched aminothiazole derivatives, which are the subject of the present invention, have excellent affinity towards CRF receptors. Furthermore, given their structure, these molecules have good dispersibility and/or solubility in solvents or solutions commonly used therapeutically which gives them pharmacological activity, and also allow the easy preparation of oral and parenteral pharmaceutical forms.

This is surprising and unexpected, since the compounds of the invention are more active in vivo than compounds of similar structure, in particular by a more significant inhibition of the response induced by CRF in the hypothalamo-hypophyso-adrenal axis.

One subject of the present invention is compounds, in racemic form or in the form of a pure enantiomer, of formula:

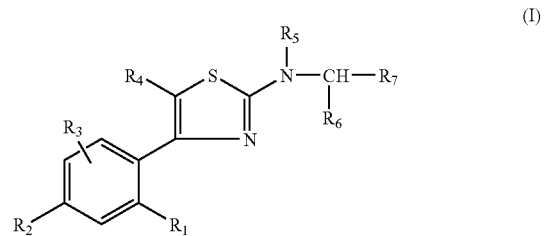

(I)

in which
$R_1$ and $R_2$, which may be identical or different, each independently represent a halogen atom; a hydroxy $(C_1-C_5)$ alkyl; a $(C_1-C_5)$alkyl; an aralkyl in which the aryl portion is $(C_6-C_8)$ and the alkyl portion is $(C_1-C_4)$; a $(C_1-C_5)$alkoxy; a trifluoromethyl group; a nitro group; a nitrile group; a group —SR in which R represents hydrogen, a $(C_1-C_5)$alkyl or an aralkyl in which the aryl portion is $(C_6-C_8)$ and the alkyl portion is $(C_1-C_4)$; a group —S—CO—R in which R represents a $(C_1-C_5)$alkyl or an aralkyl radical in which the aryl portion is $(C_6-C_8)$ and the alkyl portion is $(C_1-C_4)$; a group —COORa in which Ra represents hydrogen or a $(C_1-C_5)$alkyl; a group —CONRaRb with Ra and Rb as defined above for Ra; a group —NRaRb with Ra and Rb as defined above for Ra; a group —CONRcRd or —NRcRd in which Rc and Rd constitute, with the nitrogen atom to which they are attached, a 5- to 7-membered heterocycle; or a group —NHCO—NRaRb with Ra and Rb as defined above for Ra;

$R_3$ represents hydrogen or is as defined above for $R_1$ and $R_2$;

or alternatively $R_2$ constitutes with $R_3$, when the latter substitutes the phenyl in position 5, a group —X—CH$_2$—X— in which X independently represents a CH$_2$ or an oxygen or sulphur atom;

$R_4$ represents hydrogen, a $(C_1-C_5)$alkyl; a hydroxymethyl group; a formyl group; a halogen atom; or a $(C_3-C_5)$ cycloalkyl group;

$R_5$ represents an alkynyl of 3 to 6 carbon atoms; an alkynyl of 3 to 6 carbon atoms; a cyano $(C_1-C_6)$alkyl; a $(C_1-C_4)$ alkoxy;

$R_6$ represents a $(C_1-C_6)$alkyl; a $(C_1-C_6)$alkoxy$(C_1-C_3)$ alkyl; a $(C_3-C_5)$cycloalkyl; a $(C_3-C_6)$cycloalkyl$(C_1-C_6)$ alkyl; a $(C_1-C_6)$alkylthio$(C_1-C_3)$alkyl; a $(C_1-C_6)$alkyl-sulphoxy$(C_1-C_3)$alkyl; a $(C_1-C_6)$alkylsulphodioxy$(C_1-C_3)$alkyl;

$R_7$ represents a phenyl which is unsubstituted, mono-, di- or trisubstituted in position 3, 4 or 5 with a halogen, with a $(C_1-C_5)$alkyl, with an —O—CH$_2$—O— group on two neighbouring carbon atoms of the phenyl, with a —CF$_3$, —NO$_2$ or —CN, with a group —COOR$_8$ or —CONR$_8$R$_9$ or with a group —CH$_2$OR$_8$ in which R$_8$ and R$_9$ represent a $(C_1-C_3)$alkyl, OR$_{10}$ in which R$_{10}$ represents a $(C_1-C_5)$alkyl; or alternatively R$_7$ represents a pyridyl, thiophene, pyrazolyl, imidazolyl, $(C_3-C_5)$cycloalkyl or $(C_3-C_6)$cycloalkyl$(C_1-C_6)$alkyl group;

the addition salts thereof, the hydrates thereof and/or the solvates thereof.

In the present description, the alkyl groups and the alkoxy groups are linear or branched.

The term "halogen atom" means a fluorine, chlorine, bromine or iodine atom.

The heterocycles defined for $R_7$ can optionally be substituted with the same substituents as those on the phenyl.

According to another of its aspects, the invention relates to compounds, in racemic form or in the form of a pure enantiomer, of formula (I) in which:

$R_1$ and $R_2$, which may be identical or different, each independently represent a halogen atom; a $(C_1-C_5)$alkyl; a $(C_1-C_5)$alkoxy;

$R_3$ represents hydrogen or is as defined above for $R_1$ and $R_2$;

$R_4$ represents a $(C_1-C_5)$alkyl group;

$R_5$ represents an alkenyl of 3 to 6 carbon atoms; an alkynyl of 3 to 6 carbon atoms;

$R_6$ represents a $(C_1-C_6)$alkyl; a $(C_1-C_6)$alkoxy$(C_1-C_3)$alkyl; a $(C_3-C_5)$cycloalkyl; a $(C_3-C_6)$cycloalkyl$(C_1-C_6)$alkyl;

$R_7$ represents a phenyl which is unsubstituted or mono- or disubstituted in position 3 or 4 with a halogen, a $(C_1-C_5)$ alkyl group, a group —$CH_2OR_8$ in which $R_8$ represents a $(C_1-C_3)$alkyl or with an —O—$CH_2$—O— group in position 3, 4; or alternatively $R_7$ represents a $(C_3-C_5)$ cycloalkyl group;

the addition salts thereof, the hydrates thereof and/or the solvates thereof.

According to another of its aspects, a subject of the invention is compounds, in racemic form or in the form of a pure enantiomer, of formula:

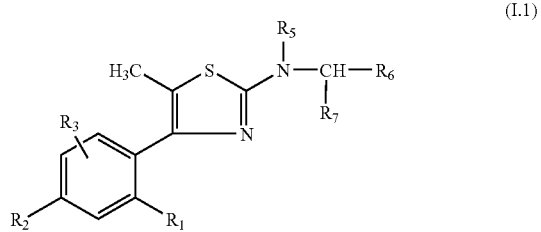

(I.1)

and in which $R_1$, $R_2$, $R_3$, $R_5$, $R_6$ and $R_7$ are as defined for (I), as well as the addition salts thereof, the hydrates thereof and/or the solvates thereof.

Among these compounds, the ones more particularly preferred are compounds, in racemic form or in the form of a pure enantiomer, of formula (I.2)

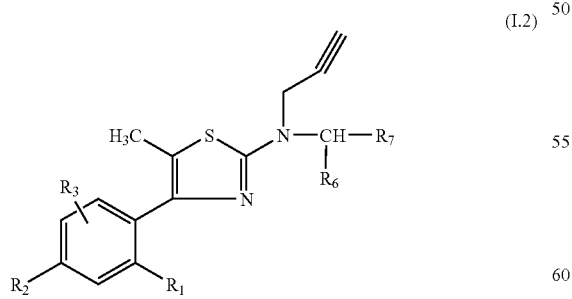

(I.2)

in which $R_1$, $R_2$, $R_3$, $R_6$ and $R_7$ are as defined for (I), as well as the addition salts thereof, the hydrates thereof and/or the solvates thereof.

The invention also relates to the compounds of formulae (I), (I.1) and (I.2), in racemic form or in the form of a pure enantiomer, in which $R_3$ is in position 5 of the phenyl, as well as the addition salts thereof, the hydrates thereof and/or the solvates thereof.

According to another of its aspects, the invention relates to compounds chosen from:

[4-(2-chloro-4-methoxy-5-methylphenyl)-5-methylthiazol-2-yl][(1R)-(1-(3-fluoro-4-methylphenyl)-2-methoxyethyl)]prop-2-ynylamine hydrochloride (Example 31)

[4-(2-chloro-4-methoxy-5-methylphenyl)-5-methylthiazol-2-yl][(1S)-(1-phenylbutyl)]prop-2-ynylamine hydrochloride (Example 33)

[4-(2-chloro-4-methoxy-5-methylphenyl)-5-methylthiazol-2-yl][(1S)-(2-cyclopropyl-1-phenylethyl)]prop-2-ynylamine hydrochloride (Example 34)

[4-(2-chloro-4-methoxyphenyl)-5-methylthiazol-2-yl] [(1S)-(2-cyclopropyl-1-phenylethyl)]prop-2-ynylamine hydrochloride (Example 35)

[4-(2-chloro-4-methoxy-5-methylphenyl)-5-methylthiazol-2-yl][(1S)-(2-cyclopropyl-1-(4-fluorophenyl) ethyl)]prop-2-ynylamine hydrochloride (Example 36)

[4-(2-chloro-4-methoxy-5-methylphenyl)-5-methylthiazol-2-yl][(1S)-(1-phenylpentyl)]prop-2-ynylamine hydrochloride (Example 37)

[4-(2-chloro-4-methoxy-5-methylphenyl)-5-methylthiazol-2-yl][(1R)-(2-methoxy-1-(4-methoxymethylphenyl)ethyl)]prop-2-ynylamine hydrochloride (Example 40)

[4-(2-chloro-4-methoxy-5-methylphenyl)-5-methylthiazol-2-yl][(1S)-(1-(4-methoxymethylphenyl)pentyl)] prop-2-ynylamine hydrochloride (Example 42)

[4-(2-chloro-4-methoxy-5-methylphenyl)-5-methylthiazol-2-yl][(1S)-(1-(4-fluorophenyl)pentyl)]prop-2-ynylamine hydrochloride (Example 45)

[4-(2-chloro-4-methoxy-5-methylphenyl)-5-methylthiazol-2-yl][(1S)-(cyclopropylphenylmethyl)]prop-2-ynylamine hydrochloride (Example 47)

[4-(2-chloro-4-methoxy-5-methylphenyl)-5-methylthiazol-2-yl][(1S)-(1(3-fluoro-4-methylphenyl)pentyl)] prop-2-ynylamine hydrochloride (Example 49)

[4-(2-chloro-4-methoxy-5-methylphenyl)-5-methylthiazol-2-yl][(1S)-(2-cyclopropyl-1-(3-fluoro-4-methylphenyl)ethyl)]prop-2-ynylamine hydrochloride (Example 50)

[4-(2-chloro-4-methoxy-5-methylphenyl)-5-methylthiazol-2-yl][(1S)-(1-(4-fluorophenyl)butyl)]prop-2-ynylamine hydrochloride (Example 51)

[4-(2-chloro-4-methoxy-5-methylphenyl)-5-methylthiazol-2-yl][(1S)-(1-(3-fluoro-4-methoxymethylphenyl) butyl)]prop-2-ynylamine hydrochloride (Example 52)

[4-(2-chloro-4-methoxy-5-methylphenyl)-5-methylthiazol-2-yl][(1S)-(2-cyclopropyl-1-(4-chlorophenyl) ethyl)]prop-2-ynylamine hydrochloride (Example 53)

[4-(2-chloro-4-methoxy-5-methylphenyl)-5-methylthiazol-2-yl][(1S)-(2-cyclopropyl-1-(4-methylphenyl) ethyl)]prop-2-ynylamine hydrochloride (Example 36)

[4-(2-chloro-4-methoxy-5-methylphenyl)-5-methylthiazol-2-yl][(1S)-(2-cyclobutyl-1-(4-fluorophenyl) ethyl)]prop-2-ynylamine hydrochloride (Example 55)

[4-(2-chloro-4-methoxy-5-methylphenyl)-5-methylthiazol-2-yl][(1S)-(2-cyclopropyl-1-(4-bromophenyl) ethyl)]prop-2-ynylamine hydrochloride (Example 56)

[4-(2-chloro-4-methoxy-5-methylphenyl)-5-methylthiazol-2-yl][(1S)-(2-cyclopropyl-1-(3,4-methylenedioxyphenyl)ethyl)]prop-2-ynylamine hydrochloride (Example 57)

[4-(2-chloro-4-methoxyphenyl)-5-methylthiazol-2-yl]
[(1S)-(2-cyclopropyl-1-(3-fluoro-4-methylphenyl)
ethyl)]prop-2-ynylamine hydrochloride (Example 58)

[4-(2,4-dimethoxy-5-methylphenyl)-5-methylthiazol-2-
yl][(1S)-(2-cyclopropyl-1-(3-fluoro-4-methylphenyl)
ethyl)]prop-2-ynylamine hydrochloride (Example 59)

[4-(4-methoxy-2,5-dimethylphenyl)-5-methylthiazol-2-
yl][(1S)-(2-cyclopropyl-1-(3-fluoro-4-methylphenyl)
ethyl)]prop-2-ynylamine hydrochloride (Example 60)

[4-(2-chloro-4-methoxy-5-methylphenyl)-5-methylthi-
azol-2-yl][(1S)-(1-(3,4-methylenedioxyphenyl)butyl)]
prop-2-ynylamine hydrochloride (Example 61)

as well as the corresponding bases, the other addition salts and the solvates and/or hydrates thereof.

The compounds of the invention in free form generally have weakly basic properties. However, depending on the nature of the substituents, some of them may show acidic properties.

The salts of the compounds of formula (I) with pharmaceutically acceptable acids or bases (when this is possible) are the preferred salts, but those which may allow the compounds of formula (I) to be isolated, in particular to be purified or to obtain pure isomers, also form a subject of the invention.

Among the pharmaceutically acceptable acids for the preparation of the addition salts to the compounds of formula (I), mention may be made of hydrochloric acid, hydrobromic acid, phosphoric acid, fumaric acid, citric acid, oxalic acid, sulphuric acid, ascorbic acid, tartaric acid, maleic acid, mandelic acid, methanesulphonic acid, lactobionic acid, gluconic acid, glucaric acid, succinic acid, sulphonic acid and hydroxypropanesulphonic acid.

Among the pharmaceutically acceptable bases for the preparation of the addition salts to the compounds of formula (I), when these compounds have acidic properties, mention may be made of sodium hydroxide, potassium hydroxide and ammonium hydroxide.

The compounds according to the invention and the intermediates which are useful for preparing them are prepared according to methods that are well known to those skilled in the art, in particular according to EP 576 350 and EP 659 747.

The reaction scheme below illustrates one preparation process for synthesizing the compounds (I).

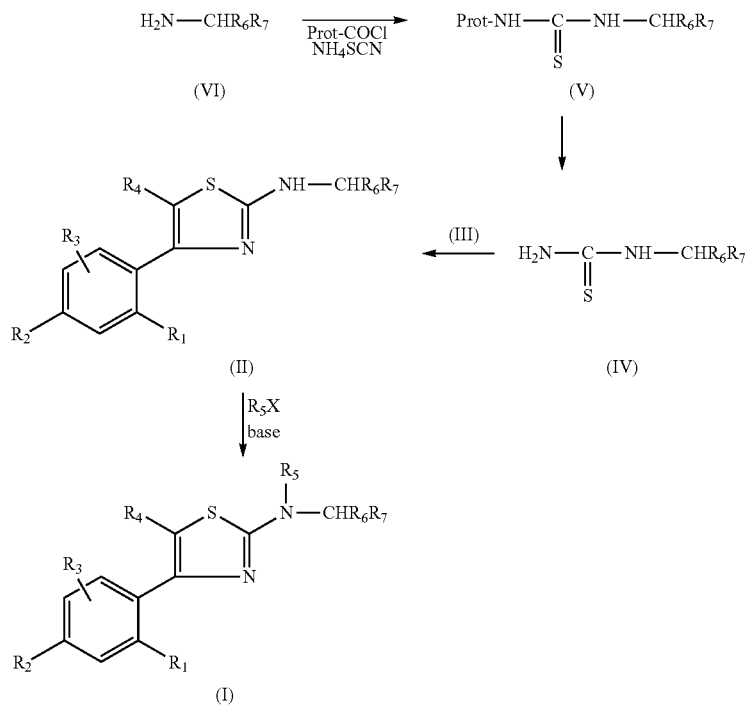

According to another of its aspects, a subject of the present invention is also a process for preparing compounds of formula (I), characterized in that an alpha-halo derivative, preferably an alpha-bromo or alpha-chloro derivative, of formula (III)

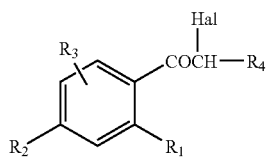

in which $R_1$, $R_2$, $R_3$ and $R_4$ are as defined for (I) and Hal represents a halogen atom, preferably bromine or chlorine, is reacted with a thiourea of formula:

in which $R_6$ and $R_7$ are as defined for (I), to give a compound of formula (II)

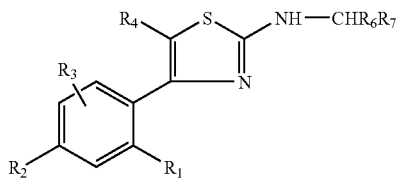

in which $R_1$, $R_2$, $R_3$, $R_4$, $R_6$ and $R_7$ are as defined for (I), in order then to subject it to an alkylation reaction to give the compound (I).

The alkylation reactions used in the above process are carried out under the usual conditions known to those skilled in the art, by the action of a suitable alkylating agent such as, for example, an alkenyl or alkynyl halide in the presence of a base, preferably sodium hydride.

The derivatives of formula (III) can be obtained from the corresponding non-halogenated ketones of formula

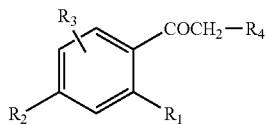

in which $R_1$, $R_2$, $R_3$ and $R_4$ are as defined for (I), either (i) by the action of bromine in a suitable organic solvent, such as acetic acid, carbon tetrachloride or diethyl ether, or (ii) by the action of quarternary ammonium tribromides according to the method described in Bull. Chem. Soc. Japan, 1987, 60, 1159-1160 and 2667-2668, or (iii) alternatively by the action of cupric bromide in an organic solvent, such as a mixture of chloroform and ethyl acetate, according to J. Org. Chem. 1964, 29, 3451-3461. As a variant, the compounds of formula (III) can be obtained by the action of 2-bromopropionyl bromide on a substituted benzene of formula:

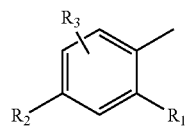

in which $R_1$, $R_2$ and $R_3$ are as defined for (I), by a Friedel-Crafts reaction.

The ketones mentioned above are generally known products or commercially-available products. These compounds can be prepared by Friedel-Crafts reaction, in the presence of a Lewis acid, according to methods that are well known to those skilled in the art.

The thiourea derivatives (IV) are obtained from protected thiourea derivatives (V)

$$\text{Prot-NH}-\underset{\underset{S}{\|}}{C}-\text{NH}-\text{CHR}_6\text{R}_7 \quad (V)$$

in which Prot represents a protecting group, for example benzoyl or pivaloyl, $R_6$ and $R_7$ being as defined previously for (I), either by a basic treatment, preferably using aqueous ammonia, sodium hydroxide or hydrazine at a temperature ranging from room temperature to the reflex point of the reaction mixture, or by means of an acid treatment preferably using hydrochloric acid.

The compounds of formula (V) are prepared by reacting, according to known methods, an isothiocyanate, for example a benzoyl isothiocyanate or a pivaloyl isothiocyanate, with the corresponding amines of formula (VI):

$$H_2N-CHR_6R_7 \quad (VI)$$

in which $R_6$ and $R_7$ are as defined for (I).

The preparation of the optically active aminothiazoles, i.e. the products in the form of pure enantiomers, is carried out starting with optically active primary amines according to Scheme 2 below by a process which is identical to that described above.

SCHEME 2

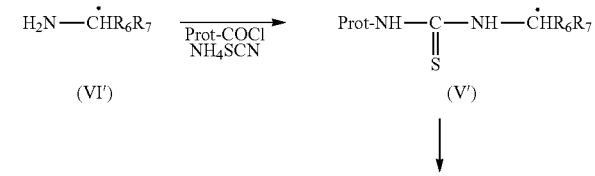

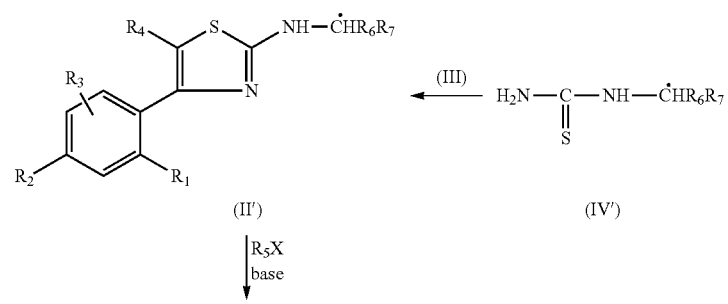

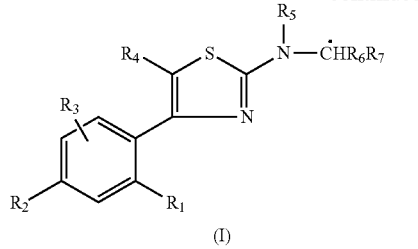

(I)

The compounds of formula (I) above also comprise those in which one or more hydrogen or carbon atoms have been replaced with their radioactive isotope, for example tritium or carbon-14. Such labelled compounds are useful in research, metabolism or pharmacokinetic studies, or alternatively in biochemical assays as receptor ligands.

The compounds of the present invention have undergone biochemical and pharmacological studies. They show highly advantageous pharmacological properties. The compounds of the invention displace, at concentrations of less than 10 μM, the binding of CRF or of related iodinated peptides (urotensine, sauvagine), for example $^{125}$I-tyrosine CRF, to the receptors present on brain membranes or on cells in culture, according to the method described by E. B. De Souza (J. Neurosci., 1987, 7, 1, 88-100).

The antagonist activity of the compounds according to the invention was demonstrated by their ability to inhibit certain activities associated with CRF. In particular, the compounds of formula (I) are capable of inhibiting the secretion of adrenocorticotropic hormone (ACTH) induced by CRF. The study on the secretion of ACTH induced by CRF was carried out, in vivo on conscious rates, according to a method adapted from C. Rivier et al., Endocrinology, 1982, 110 (1), 272-278.

CRF is a neuropeptide which controls the activity of the hypothalamo-hypophyso-adrenal axis. This factor is responsible for stress-related behavioural and endocrine responses. Specifically, it has been demonstrated that CRF can modulate behaviour and also certain functions of the autonomic nervous system (G. F. Koob, F. E. Bloom, Fed. Proc., 1985, 44, 259; M. R. Brown, L. A. Fisher, Fed. Proc., 1985, 44, 243). More particularly, CRF induces the secretion of corticotropin (ACTH), β-endorphins and other peptides derived from pro-opiomelanocortin (A. Tazi et al., Régul. Peptides, 1987, 18, 37; M. R. Brown et al., Regul. Peptides, 1986, 16, 321; C. L. Williams et al., Am. J. Physiol., 1987, G 582, 253).

The compounds of the invention may thus be useful in regulating the secretion of these endogenous substances. They find their applications more especially as active principles of medicinal products for reducing the response to stress (behaviour, emotional states, gastrointestinal and cardiovascular disorders, disorders of the immune system) and more generally in pathologies involving CRF, for example psychiatric disorders, anxiety, depression, anorexia nervosa, epilepsy, sexual activity disorders and fertility disorders, Alzheimer's disease or the like.

The compounds of the invention are very stable and are thus particularly suitable for forming the active principle of medicinal products.

The invention also extends to a pharmaceutical compositions containing, as active principle, a compound of formula (I) or one of the pharmaceutically acceptable salts thereof, optionally in combination with one or more inert and suitable excipients.

In each dosage unit, the active principle of formula (I) is present in amounts that are suited to the daily doses envisaged. Each dosage unit is appropriately adjusted according to the dosage and the type of administration envisaged, for example tablets, gel capsules and the like, sachets, ampoules, syrups and the like, drops, transdermal or transmucosal patches, such that such a dosage unit contains 0.5 mg to 800 mg of active principle, preferably 0.5 mg to 200 mg.

The compounds according to the invention can also be used in combination with another active principle which is useful for the desired treatment, such as, for example, anxiolytic agents, antidepressants or anorexigenic agents.

The compound of formula (I) are relatively non-toxic; their toxicity is compatible with their use as medicinal products for treating the above disorders and diseases.

The compounds of formula (I) can be formulated in pharmaceutical compositions for administration to mammals, including man, for the treatment of the abovementioned diseases.

The pharmaceutical compositions thus obtained are advantageously in various forms such as, for example, injectable or drinkable solutions, sugar-coated tablets, tablets or gel capsules. The pharmaceutical compositions containing, as active principle, at least one compound of formula (I) or one of the salts thereof are useful in particular for preventively or curatively treating stress-related conditions and more generally in the treatment of any pathology involving CRF, such as, for example: Cushing's disease, neuropsychiatric disorders such as depression, anxiety, panic, obsessive compulsive disorders, mood disorders, post-traumatic stress, behavioral disorders, aggressiveness, anorexia, bulimia, hyperglycemia, premature labor, at-risk pregnancy, retarded growth, sleeping disorders, epilepsy, and all types of depression; Alzheimer's disease, Parkinson's disease, Huntington's chorea; amyotrophic lateral sclerosis; vascular, cardiac and cerebral disorders; sexual activity disorders and fertility disorders; immunodepression, immunosuppression, inflammatory processes, multiple infections, rheumatoid arthritis, osteoarthritis, uveitis, psoriasis and diabetes; cancers; gastrointestinal functional disorders and inflammations arising therefrom (irritable and inflammatory bowel, diarrhoea); pain-perception disorders, fibromyalgias which may or may not be associated with sleeping disorders, fatigue, migraine; symptoms associated with (alcohol) dependency and withdrawal from drugs.

The dosage can vary widely as a function of the age, weight and state of health of the patient, the nature and seriousness of the complaint, as well as the route of administration. This dosage comprises the daily administration of one or more doses of approximately from 0.5 to 800 mg, preferably approximately from 0.5 to 200 mg.

In the pharmaceutical compositions of the present invention for oral, sublingual, subcutaneous, intramuscular, intravenous, transdermal, transmucosal, local or rectal administration, the active principle can be administered in unit forms of administration, as a mixture with conventional pharmaceutical supports, to animals and to human beings. The appropriate unit forms of administration comprise oral-route forms such as tablets, gel capsules, powders, granules and oral solutions or suspensions, sublingual and buccal administration forms, subcutaneous, intramuscular, intravenous, intranasal or intraocular administration forms and rectal administration forms.

When a solid composition is prepared in the form of tablets, the main active principle is mixed with a pharmaceutical vehicle such as gelatin, starch, lactose, magnesium stearate, talc, gum arabic or the like. The tablets can be coated with sucrose or other suitable materials, or alternatively they can be treated such that they have sustained or delayed activity and such that they continuously release a predetermined amount of active principle.

A preparation as gel capsules is obtained by mixing the active principle with a diluent and pouring the mixture obtained into soft or hard gel capsules.

A preparation in syrup or elixir form can contain the active principle together with a sweetener, preferably a calorie-free sweetener, methyl paraben and propyl paraben as antiseptic agents, as well as a flavour enhancer and a suitable colorant.

The water-dispersible powders or granules can contain the active principle as a mixture with dispersants or wetting agents, or suspending agents, such as polyvinylpyrrolidone, as well as with sweeteners or flavour enhancers.

For rectal administration, use is made of suppositories which are prepared with binders that melt at the rectal temperature, for example cocoa butter or polyethylene glycols.

Aqueous suspensions, isotonic saline solutions or sterile, injectable solutions which contain pharmaceutically compatible dispersants and/or wetting agents, for example propylene glycol or butylene glycol, are used for parental, intranasal or intraocular administration.

For transmucosal administration, the active principle can be formulated in the presence of a promoter such as a bile salt, a hydrophilic polymer such as, for example, hydroxypropylcellulose, hydroxypropylmethylcellulose, hydroxyethylcellulose, ethylcellulose, carboxymethylcellulose, dextran, polyvinylpyrrolidone, pectins, starches, gelatin, casein, acrylic acids, acrylic esters and copolymers thereof, vinyl polymers or copolymers, vinyl alcohols, alkoxy polymers, polyethylene oxide polymers, polyethers or a mixture thereof.

The active principle can also be formulated in the form of microcapsules, optionally with one or more supports or additives.

The active principle can also be in the form of a complex with a cyclodextrin, for example α-, β- or γ-cyclodextrin, 2-hydroxypropyl-β-cyclodextrin or methyl-β-cyclodextrin.

The examples which follow, which are given in a non-limiting manner, illustrative the invention.

The method for synthesizing the various intermediates for obtaining the compounds of the invention are described in preparations. These intermediates are all obtained according to methods that are well known to those skilled in the art.

The melting points were measured according to the Micro-Köfler technique and are expressed in degrees Celsius.

The proton nuclear magnetic resonance ($^1$H NMR) spectra were acquired in $CDCl_3$ except where other wise mentioned, at 200 MHz or at 300 MHz. The chemical shifts are expressed in p.p.m. and the coupling constants are expressed in Hertz.

The enantiomeric excesses (ee) are evaluated from the chromatograms obtained either by chiral-phase HPLC chromatography or by supercritical fluid chiral (SFC) chromatography.

The optical rotations of the optically active products are characterized by their $[\alpha]^t{}_D$ (the concentrations c of the solutions analysed are expressed in grams per 100 ml).

The abbreviations used below are as follows: s=singlet; m=multiplet; d=doublet; t=triplet; q=quartet.

The compounds of the invention give an elemental analysis in accordance with the theoretical result.

The compounds of the invention described in Tables 3 and 5 also give NMR spectra that are in accordance with their structure.

PREPARATION OF THE α-BROMO KETONES OF FORMULA (III)

2-Bromo-1-(2-chloro-4-methoxy-5-methylphenyl)propan-1-one Compound III.1

A solution of 46 g (280 mmol) of 4-chloro-2-methoxytoluene in 150 ml of dichloromethane is stirred at 0° C. and 29.4 g (280 mmol) of 2-bromopropionyl bromide are added. 39.2 g (294 mmol) of aluminium trichloride are added portionwise to the mixture. This mixture is stirred while allowing the temperature to rise gradually to room temperature. After stirring for 4 hours, the reaction mixture is poured slowly onto ice. 50 ml of 1N of hydrochloric acid and 1 liter of water are added to this stirred mixture, followed by extraction with 1.2 liters of tert-butyl methyl ether. The organic phase is washed with water, with saturated aqueous sodium-hydrogen carbonate solution, with water and then with saturated sodium chloride solution. It is dried over anhydrous sodium sulphate and then evaporated to dryness. The crude residue is purified by chromatography on silica gel (solvent: 50/1 cyclohexane/ethyl acetate). 67 g of compound III-1 are obtained. Yield=82%.

$^1$H NMR: 7.44 (s, Ar, 1H); 6.86 (s, Ar, 1H); 5.41 (q, J=5.35 Hz, CH, 1H); 3.90 (s, $OCH_3$, 3H); 2.23 (s, $CH_3$, 3H); 1.91 (d, J=5.35 Hz, $CH_3$, 3H).

The following compounds were synthesized by the same method:

2-Bromo-1-(2-chloro-4-methoxyphenyl)propan-1-one Compound III.2

2-Bromo-1-(2,4-dichloro-5-methylphenyl)propan-1-one, Compound III.3

2-Bromo-1-(2,4-dimethoxy-5-methylphenyl)propan-1-one Compound III.4

2-Bromo-1-(4-methoxy-2,5-dimethylphenyl)propan-1-one Compound III.5

PREPARATION OF THE RACEMIC AMINES OF FORMULA (VI)

First Method a) 2-Amino-2-(4-fluorophenyl)ethanol Compound I.1

60 ml (60 mmol) of a 1M solution of lithium aluminium hydride in tetrahydrofuran are stirred at reflux, followed by portionwise addition of 5 g (29 mmol) of 4-fluoro-DL-α-phenylglycine (Fluka). After stirring at reflux for six hours, the reaction mixture is stirred at 0° C., followed by slow addition of 2.5 ml of water, 2.5 ml of aqueous 15% sodium hydroxide solution and then 7.5 ml of water. The suspension obtained is filtered through Celite. The filtrate is concentrated and taken up in 300 ml of dichloromethane. The solution is washed with saturated sodium chloride solution, dried over anhydrous sodium sulphate and then evaporated to dryness. 3.3 g of an oily yellow product are obtained. Yield=73%.

MS ($MH^+$=156)

$^1$H NMR: 7.23-7.33 (m, Ar, 2H); 6.95-7.07 (m, Ar, 2H); 4.08 (m, CH, 1H); 3.45-3.86 (m, $CH_2O$, 2.03 (s, $NH_2$ and OH, 3H).

b) 1-(4-Fluorophenyl)-2-methoxyethylamine Compound VI.1

0.94 g (23 mmol) of potassium hydride, obtained by washing 2.2 g of an oily suspension with pentane, are suspended in 18 ml of tetrahydrofuran and stirred at 10° C. A solution of 3.3 g (21 mmol) of Compound 1.1 in 43 ml of tetrahydrofuran is added slowly. After stirring for sixteen hours at room temperature, a solution of 1.3 ml (20.8 mmol) of iodomethane in 25 mol of tetrahydrofuran is added over one hour 30 minutes. The reaction mixture is stirred for three hours at room temperature and is then poured into 300 ml of ice-cold water containing salt. The mixture is extracted with 500 ml of tert-butyl methyl ether. The organic phase is washed with water and then with saturated sodium chloride solution, dried over anhydrous sodium sulphate and then evaporated to dryness. 3.2 g of an oily amine are obtained.

Yield=88%.

$^1$H NMR: 7.24-7.38 (m, Ar, 2H); 6.93-7.05 (m, Ar, 2H); 4.16 (m, CH, 1H); 3.45 (dd, $CH_2$, 1H); 3.36 (s, $OCH_3$, 3H); 3.29 (d, $CH_2$, 1H); 1.70 (s, $NH_2$, 2H).

2-Methoxy-1-phenylethylamine, Compound VI.2, is obtained in the same way.

Second Method a) Synthesis of Substituted Phenyl Ketones. Compounds 3
Procedure A:
1-(3-Fluoro-4-methylphenyl)-2-methoxyethan-1-one Compound 3.1

To prepare the magnesium reagent, 14 g (583 mmol, 1 eq.) of magnesium shavings are left stirring in the presence of crushed glass and under argon overnight. They are covered with 400 ml of diethyl ether, followed by addition of one spatula-tipful of iodine. 110 g (582 mmol) of 4-bromo-2-fluorotoluene dissolved in 700 ml of diethyl ether are added slowly so as to maintain a gentle reflux, and the reaction misture is then heated at reflux for three hours. 39 ml of methoxyacetonitrile (610 mmol, 1.1 eq.) are added and the mixture is left to react for two hours. Once the reaction is complete, the reaction mixture is poured into 1.5 kg of ice, followed by addition of 300 ml of concentrated hydrochloric acid with stirring. This mixture is extracted with diethyl ether, dried over sodium sulphate and evaporated. 77 g of Compound 3.1 are recovered, which product is used directly in the second step without purifying it.

The following compounds are obtained in the same way:
1-(4-Chloro-3-fluorophenyl)-2-methoxyethan-1-one Compound 3.2
1-(4-Chlorophenyl)-2-methoxyethan-1-one Compound 3.3
3-Cyclopropyl-1-(4-fluorophenyl)propan-1-one Compound 3.4

Procedure B:
2-Methoxy-1-(4-methoxymethylphenyl)ethan-1-one Compound 3.5

A solution of 62 g (308 mmol) of 1-bromo-4-methoxymethylphenyl in 600 ml of tetrahydrofuran is stirred at −70° C. and 200 ml (320 mmol) of a 1.6 M solution of butyllithium are added slowly. The reaction mixture is stirred for 30 minutes at −70° C., followed by slow addition of a solution of 50 g (380 mmol) of 2-N-dimethoxy-N-methylacetamide. The reaction mixture is stirred while allowing the temperature to rise gradually to room temperature. After stirring for 4 hours, it is cooled to 0° C. and saturated aqueous ammonium chloride solution is added slowly. The mixture is extracted with ethyl acetate and the organic phase is washed with water and then with saturated sodium chloride solution, dried over anhydrous sodium sulphate and then evaporated to dryness. The residue obtained is purified by chromatography on silica gel (solvent: 9/1 and then 3/1 cyclohexane/ethyl acetate). 32 g of ketone are obtained. Yield=53%

$^1$H NMR: 7.89 (d, J=8.1 Hz, Ar, 2H); 7.40 (d, J=8.1 Hz, Ar, 2H); 4.66 (s, $OCH_2$, 2H); 4.48 (s, $OCH_2$, 2H); 3.47 (s, $CH_3$, 3H); 3.38 (s, $CH_3$, 3H)

b) Synthesis of the Oximes, Compounds 4
1-(3-Fluoro-4-methylphenyl)-2-methoxyethan-1-one Oxime Compound 4.1

Procedure A:
33 g of hydroxylamine hydrochloride (475 mmol, 1.6 eq.) are mixed with 30 ml of water and 100 ml of ethanol. 54 g (296 mmol) of Compound 3.1 diluted in 30 ml of ethanol are added at 0° C. Once the addition is complete, 60 g of pre-crushed sodium hydroxide pellets (1.5 mol, 5 eq.) are added and the temperature is kept below 30° C. The reaction mixture is left overnight at room temperature and then placed at 0° C. for neutralization with concentrated hydrochloric acid (pH<7). This mixture is then extracted with ethyl acetate and the organic phase is washed with water and with saturated sodium chloride solution. The organic phase is dried over sodium sulphate and evaporated. The oil thus obtained is chromatographed on silica gel using a 1/9 (v/v) ethyl acetate/cyclohexane mixture as eluent. 26 g of (Z) isomer and 9 g of (E) isomer are obtained, i.e. a yield Y=45% of (Z) and 16% of (E).

Procedure B:
47 g of hydroxylamine hydrochloride (676 mmol, 1.6 eq.) are mixed with 275 ml of pyridine. 77 g (423 mmol) of Compound 3.1 are added at 0° C. The reaction mixture is left for five hours at room temperature. Once the reaction is complete, the pyridine is evaporated off and the residue is then extracted with dichloromethane. The organic phase is washed with water and then with saturated sodium chloride solution. The organic phase is dried over sodium sulphate and evaporated, and the oil thus obtained is chromatographed on silica gel using a 1/9 (v/v) ethyl acetate/cyclohexane mixture as eluent, to give 42.5 g of compound (Z) and 14 g of compound (E), i.e. a yield Y=51% of Z and 17% of E.

$^1$H NMR of compound Z: 11.59 (N—OH, s, 1H); 7.20-7.40 (Ar, m, 3H); 4.51 (—O—$CH_2$—, s, 2H); 3.18 ($OCH_3$, s, 3H); 2.20 ($CH_3$-Ph, s, 3H).

$^1$H NMR of compound E: 11.30 (N—OH, s, 1H); 7.20-7.50 (Ar, m, 3H); 4.21 (—O—$CH_2$—, s, 2H); 3.17 ($OCH_3$, s, 3H); 2.22 ($CH_3$-Ph, s, 3H).

The following products are obtained in the same way by one of the two procedures mentioned above:
1-(4-Chloro-3-fluorophenyl)-2-methoxyethan-1-one oxime Compound 4.2
1-(4-Chlorophenyl)-2-methoxyethan-1-one oxime Compound 4.3
1-Phenylbutan-1-one oxime Compound 4.4
1-(4-Methoxymethylphenyl)-2-methoxyethan-1-one oxime Compound 4.5
1-(4-Methoxymethylphenyl)butan-1-one oxime Compound 4.6
Dicyclobutyl ketone oxime Compound 4.7
1-Phenylpentan-1-one oxime Compound 4.8 c) Synthesis of the Amines Compounds VI
1-(3-Fluoro-4-methylphenyl)-2-methoxyethylamine Compound VI.3

A solution of 1 g of Compound 4.1 (5 mmol) dissolved in 15 ml of tetrahydrofuran is added slowly, at 0° C., to 10 ml of a 1M solution of lithium aluminium hydride in tetrahydrofuran (10 mmol, 8 eq.). The reaction mixture is allowed to warm to room temperature and is then left to react for two hours and is refluxed for one hour. The reaction mixture is cooled to 0° C. in order to add 10 ml of water. The aqueous phase is extracted with diethyl ether. The combined organic phases are extracted with 2N hydrochloric acid solution. The acidic aqueous phase obtained is stirred at 0° C. and 35% sodium hydroxide solution is added. The alkaline solution obtained is extracted with dichloromethane. The organic phase is washed with saturated sodium chloride solution and then dried over sodium sulphate and evaporated to dryness. After filtration on silica using a 95/5 (v/v) dichloromethane/methanol mixture as eluent, 0.6 g of Compound VI.3 is obtained. Yield=65%.

$^1$H NMR: 6.90-7.20 (Ar, m, 3H); 4.14 (—CH—N, dd, J=4 and 8.5, 1H); 3.47 (—CH$_2$—O, dd, J=4 and 9, 1H); 3.37 (OCH$_3$, s, 3H); 3.32 (—CH$_2$—O, dd, 1H, J=8.5 and 9); 2.24 (CH$_3$-Ph, d, J=1.8, 3H); 1.68 (—NH$_2$, s, 2H).

The following compounds are obtained in the same way:

1-(4-Chloro-3-fluorophenyl)-2-methoxyethylamine Compound VI.4

Dicyclobutylmethylamine Compound VI.5

Third Method a) Synthesis of O-alkyloxime Compounds 6
Procedure A:
1-Phenylbutan-1-one O-methyloxime Compound 6.1

18 g (0.45 mol) of 55% sodium hydride in oil are added portionwise, at 0° C. and over one hour, to 66 g (0.40 mol) of 1-phenylbutan-1-one oxime (Compound 4.4) in a mixture of 400 ml of dimethylformamide and tetrahydrofuran (1:1). After addition of 31 ml (0.5 mol) of methyl iodide, the reaction mixture gradually becomes very thick. After addition of 50 ml of ethanol, and then water, the reaction mixture is extracted with 4×250 ml of ethyl acetate. The organic phase is washed with saturated sodium chloride solution, dried over sodium sulphate and then evaporated under vacuum. 75 g of a pale yellow oil are obtained, as a mixture of geometrical isomers (7% (Z) and 93% (E)). Yield=94% (Z+E).

These two isomers can be separated by chromatography on silica, eluting with a cyclohexane/ethyl acetate mixture.

$^1$H NMR: 7.56-7.93 (m, Ar, 2H); 7.24-7.40 (m, Ar, 3H), 3.95 [s, OCH$_3$, (E)]; 3.82 [s, OCH$_3$, (Z)]; 2.71 [m, CH$_2$, (E)]; 2.50 [m, CH$_2$, (Z)]; 1.41-1.64 (m, CH$_2$, 2H); 0.84-1.03 (m, CH$_3$, 3H).

The following alkylated oximes are obtained in the same way:

1-Phenylpentan-1-one O-methyloxime Compound 6.2
1-(4-Chlorophenyl)-2-methoxyethan-1-one O-benzyloxime Compound 6.3
2-Methoxy-1-(4-methoxymethylphenyl)ethan-1-one O-methyloxime Compound 6.4
1-(4-Methoxymethylphenyl)butan-1-one O-methyloxime Compound 6.5

Procedure B:
Cyclobutyl 4-fluorophenyl ketone O-benzyloxime Compound 6.6

A solution of 15 g (84 mmol) of cyclobutyl 4-fluorophenyl ketone in 80 ml of ethanol is stirred at room temperature and 20.2 g (126 mmol) of O-benzylhydroxylamine hydrochloride are added. 8.4 g (210 mmol) of sodium hydroxide are then added portionwise to the mixture, which is stirred for 4 hours at room temperature. Water is added to the mixture, followed by extraction with ethyl acetate. The organic phase is washed with water until neutral, and then with saturated aqueous sodium chloride solution. It is dried over sodium sulphate and then evaporated to dryness. 28.4 g of a mixture of isomers (58% E, 42% Z) are obtained.

$^1$H NMR (DMSO-d$_6$): 7.15-7.48 (m, Ar, 9H); 5.07 [s, OCH$_2$, (E)]; 5.01 [s, OCH$_2$, (Z)]; 3.68-3.82 [m, CH cyclobutyl, (E)]; 3.36-3.52 [m, CH cyclobutyl, (Z)]; 1.58-2.30 (m, CH$_2$ cyclobutyl, 6H).

The same method is used to obtain the following compound:

3-Cyclopropyl-1-(4-fluorophenyl)propan-1-one O-benzyloxime Compound 6.7 b) Synthesis of the Amines Compounds VI
1-Phenylbutylamine Compound VI.6

A solution of 14.2 g (0.085 mol) of 1-phenylbutan-1-one O-methyloxime (Compound 6.1) in 85 ml of tetrahydrofuran is added dropwise, under argon, to 85 ml of a 1M solution of lithium aluminium hydride in tetrahydrofuran. At the end of the addition, the reaction mixture is refluxed for one hour thirty minutes. After leaving overnight at room temperature, 3.5 ml of H$_2$O are added, followed by 3.5 ml of 15% sodium hydroxide and then 10.5 ml of H$_2$O. The precipitate is filtered off and washed with diethyl ether. The tetrahydrofuran/diethyl ether filtrate is washed with water and is then extracted three times with 1N hydrochloric acid solution. The acidic aqueous phases are combined and then basified at 0° C. with 35% sodium hydroxide. After extractions with dichloromethane, washes with water, drying over sodium sulphate and then evaporation under vacuum, 9.3 g of an oil are obtained. Yield=73%.

$^1$H NMR: 7.11-7.36 (m, Ar, 5H); 3.81-3.95 (m, CH, 1H); 1.73 (s, NH$_2$, 2H); 1.60-1.70 (m, CH$_2$, 2H); 1.15-1.36 (m, CH$_2$, 2H); 0.95-0.98 (m, CH$_3$, 3H).

The following amines are obtained in the same way:

1-Phenylpentylamine Compound VI.7
1-(4-Chlorophenyl)-2-methoxyethylamine Compound VI.8
2-Methoxy-1-(4-methoxymethylphenyl)ethylamine Compound VI.9
1-(4-Methoxymethylphenyl)butylamine Compound VI.10
Cyclobutyl-(4-fluorophenyl)methylamine Compound VI.11
3-Cyclopropyl-1-(4-fluorophenyl)propylamine Compound VI.12

Fourth Method 1-(4-Fluorophenyl)pentylamine Compound VI.13

A solution of 1.21 g (10 mmol) of 4-fluorobenzonitrile in 10 ml of tetrahydrofuran is stirred at 0° C. and 10 ml (10 mmol) of a 1M solution of boran-tetrahydrofuran are added dropwise. The mixture is stirred for one hour thirty minutes at room temperature and then transferred slowly into 18.8 ml of a 1.6 ml solution of butyllithium in hexane, which has been precooled to −78° C. with stirring. The reaction mixture is stirred for two hours at −78° C. and then hydrolysed at this temperature with 10 ml of 2N hydrochloric acid. The organic phase is extracted with 2N hydrochloric acid and the acidic aqueous phase obtained is neutralized at 0° C. by slow addition of 35% sodium hydroxide and then extracted with ethyl acetate. The organic phase is washed with water and then with saturated sodium chloride solution, dried over anhydrous sodium sulphate and then evaporated to dryness. 0.95 g of an oily amine is obtained. Yield=53%.

$^1$H NMR: 7.21-7.31 (m, Ar, 2H); 6.93-7.05 (m, Ar, 2H); 4.13 (t, CH, 1H); 1.59-1.75 (m, CH$_2$, 2H); 1.49 (s, NH$_2$, 2H); 1.24-1.33 (m, CH$_2$—CH$_2$, 4H); 0.85 (t, CH$_3$, 3H).

The following compound is obtained in the same way:
1-(3-Fluoro-4-methylphenyl)pentylamine Compound VI.14

Fifth Method 1-(4-Fluorophenyl)butylamine Compound VI.15

One crystal of iodine is added to a suspension of 2.4 g (100 mmol) of magnesium in 30 ml of diethyl ether, followed by 17.4 g (100 mmol) of 4-bromofluorobenzene (diluted in 70 ml of diethyl ether) so as to create a gentle reflux. The reaction mixture is refluxed for one hour and then cooled to room temperature and 5.75 g (85 mmol) of butyronitrile diluted in 30 ml of diethyl ether are added. The reaction mixture is refluxed for two hours and then cooled and filtered through glass wool. The filtrate is stirred at room temperature and 100 ml (100 mmol) of a 1M solution of lithium aluminium hydride in tetrahydrofuran are added slowly. The reaction mixture is refluxed for eighteen hours and then cooled to 0° C., followed by successive addition of 3.8 ml of water, 3.8 ml of 15% sodium hydroxide and then 11.4 ml of water. The mixture is filtered through Celite and the filtrate is evaporated to dryness. The residue obtained is filtered through silica, eluting with 98/2 (v/v) dichloromethane/methanol. 6.3 g of an oily product are obtained. Yield=37%.

$^1$H NMR: 7.22-7.36 (m, Ar, 2H); 6.92-7.05 (m, Ar, 2H); 3.87 (t, CH, 1H); 1.45-1.65 (m, CH$_2$, 2H); 1.12-1.40 (m, CH$_2$, 2H); 0.88 (t, CH$_3$, 3H).

PREPARATION OF THE RACEMIC THIOUREAS COMPOUNDS IV

N[1-(4-Fluorophenyl)-2-methoxyethyl]thiourea Compound IV.1

6.5 ml (56.6 mmol) of benzoyl chloride are added, at 0° C., to a stirred solution of 4.5 g (58 mmol) of ammonium isothiocyanate in 115 ml of acetone. After thirty minutes, 8.6 g (56 mmol) of Compound VI.1 dissolved in 100 ml of acetone are added slowly. The reaction mixture is stirred for two hours at room temperature and then concentrated under educed pressure. The suspension is taken up in 200 ml of tert-butyl methyl ether and 200 ml of water. The organic phase is washed with water and then with saturated sodium chloride solution, dried over anhydrous sodium sulphate and then evaporated to dryness. The evaporation residue is dissolved in 180 ml of ethanol and 5.85 ml (116 mmol) of hydrazine monohydrate are added to the solution obtained. After stirring for sixteen hours at room temperature, since the reaction is incomplete, a further 1.7 ml of hydrazine are added. After stirring for 24 hours at room temperature, the reaction mixture is evaporated. The evaporation residue is dissolved in 500 ml of ethyl acetate and the organic phase is washed with water and then with saturated sodium chloride solution, dried over anhydrous sodium sulphate and evaporated to dryness. The evaporation residue is chromatographed on a column of silica, eluting with 1/1 (v/v) cyclohexane/ethyl acetate. 8.5 g (40 mmol) of white solid product are obtained. Yield=69%. m.p.=154° C.

$^1$H NMR (DMSO-d$_6$): 8.10 (d, NH, 1H); 7.28-7.32 (m, Ar, 2H); 7.08-7.17 (m, Ar and NH$_2$, 4H); 5.45 (m, CH, 1H); 3.54-3.62 (m, CH—CH$_2$, 2H); 3.24 (s, OCH$_3$, 3H).

The following thioureas described in Table 1 are obtained in the same way:

TABLE 1

$$H_2N-\underset{\underset{S}{\|}}{C}-NH-CHR_6R_7 \quad (IV)$$

| COMPOUNDS | R$_7$ | R$_6$ | m.p. ° C.; NMR; Mass |
|---|---|---|---|
| IV.2 | phenyl | —CH$_2$OCH$_3$ | 137 |
| IV.3 | 3-fluoro-4-methylphenyl | —CH$_2$OCH$_3$ | 186 |
| IV.4 | phenyl | —(CH$_2$)$_3$CH$_3$ | 138 |
| IV.5 | phenyl | —(CH$_2$)$_2$CH$_3$ | 118 |

TABLE 1-continued $$H_2N-\underset{S}{\overset{\parallel}{C}}-NH-CHR_6R_7 \quad (IV)$$

| COMPOUNDS | R$_7$ | R$_6$ | m.p. ° C.; NMR; Mass |
|---|---|---|---|
| IV.6 | 4-(CH$_2$OCH$_3$)-phenyl | —CH$_2$OCH$_3$ | MS(MH+)255 $^1$H RMN: 7.24-7.52(m, Ar, 4H); 7.0(m, NH, 1H); 6.02(s, NH$_2$, 2H): 4.70(m, CH, 1H); 4.42(s, OCH$_2$, 2H); 3.60(m, OCH$_2$, 2H); 3.37(s, OCH$_3$, 3H); 3.34(s, OCH$_3$, 3H). |
| IV.7 | 4-(CH$_2$OCH$_3$)-phenyl | —(CH$_2$)$_2$CH$_3$ | MS(MH+)253 $^1$H RMN: 7.22-7.34(m, Ar, 4H); 6.73(m, NH, 1H); 5.64(m, NH$_2$, 2H); 4.41(s, OCH$_2$, 2H); 4.40(m, CH, 1H): 3.38(s, OCH$_3$, 3H); 1.68-1.82(m, CH$_2$, 2H); 1.16-1.40(m, CH$_2$, 2H); 0.89(t, J = 7 Hz, CH$_3$, 3H). |
| IV.8 | 4-F-phenyl | —(CH$_2$)$_3$CH$_3$ | 154 |
| IV.9 | 3-F-4-CH$_3$-phenyl | —(CH$_2$)$_3$CH$_3$ | 145 |
| IV.10 | 4-F-phenyl | —(CH$_2$)$_2$CH$_3$ | 107 |
| IV.11 | 4-Cl-phenyl | —CH$_2$OCH$_3$ | $^1$H RMN: 7.23-7.40(m, Ar, 4H); 6.80(d, NH, 1H); 5.87(s, NH$_2$, 2H); 4.90(m, CH, 1H); 3.62(m, OCH$_2$, 2H); 3.35(s, OCH$_3$, 3H). |
| IV.12 | cyclobutyl | cyclobutyl | 144 |

US 8,420,679 B2

TABLE 1-continued $$H_2N-\underset{\underset{S}{\|}}{C}-NH-CHR_6R_7 \quad (IV)$$

| COMPOUNDS | R₇ | R₆ | m.p. ° C.; NMR; Mass |
|---|---|---|---|
| IV.13 | 3-F,4-Cl-phenyl | —CH₂OCH₃ | 109 |
| IV.14 | 4-F-phenyl | cyclobutylmethyl | ¹H RMN: 7.19-7.29(m, Ar, 2H); 6.98-7.08(m, Ar, 2H); 6.83(s, NH, 1H); 5.75(m, NH₂, 2H); 4.40(m, CH, 1H); 2.50-2.60(m, CH, 1H).; 2.09-2.15(m, CH d'un CH₂, 1H).; 1.68-1.95(m, CH₂, 5H). |
| IV.15 | 4-F-phenyl | —(CH₂)₂-cyclopropyl | ¹H RMN: 7.19-7.30(m, Ar, 2H); 7.02-7.11(m, Ar, 2H); 6.50(s, NH, 1H); 5.55(s, NH₂, 2H); 4.40-4.60(m, CH, 1H); 1.82-2.00(m, CH₂, 2H).; 1.15-1.35(m, CH₂, 2H).; 0.55-0.75(m, CH cyclopropyle, 1H); 0.38-0.50(m, CH₂ cyclopropyle, 2H); 0.01-0.09(m, CH₂ cyproyle, 2H). |

PREPARATION OF THE NH THIAZOLES COMPOUNDS II

[4-(2-Chloro-4-methoxy-5-methylphenyl)-5-methylthiazol-2-yl]-[1-(4-methoxymethylphenyl)butyl]amine Compound II.1

1.92 g (6 mmol) of 2-bromo-1-(2-chloro-4-methoxy-5-methylphenyl)propan-1-one (Compound III.1) and 1.5 ml of triethylamine are added to 1.4 g (5.54 mmol) of 1-(4-methoxymethylphenyl)butylthiourea (Compound IV.7) in 60 ml of ethanol. The reaction mixture is stirred at 85° C. for three hours and then concentrated under reduced pressure. The residue is taken up in 100 ml of dichloromethane and 50 ml of water. The organic phase is washed with saturated aqueous sodium chloride solution, dried over sodium sulphate and then evaporated to dryness under vacuum. The crude extract is purified by chromatography on a column of silica gel, eluting with 9/1 (v/v) cyclohexane/ethyl acetate. 2.35 g of aminothiazole are obtained. Yield=96%.

MS(MH⁺)=445

¹H NMR: 7.26-7.36 (m, Ar, 4H); 7.10 (s, Ar, 1H); 6.83 (s, Ar, 1H); 5.44-5.47 (m, NH, 1H); 4.43 (s, OCH₂, 2H); 4.17-4.33 (m, CH, 1H); 3.81 (s, OCH₃, 3H); 3.39 (s, OCH₃, 3H); 2.14 (s, CH₃, 3H); 2.05 (s, Ch₃, 3H); 1.63-1.88 (m, CH₂, 2H); 1.23-1.48 (m, CH₂, 2H); 0.90 (t, CH₃, 3H).

The following products described in Table 2 were prepared in the same way:

TABLE 2

(II)

Structure: thiazole with H₃C at 5-position, S and N ring atoms, NH—CH(R₇)—R₆ at 2-position, and substituted phenyl (R₁, R₂, R₃) at 4-position.

| COMPOUNDS | R₁/R₂/R₃ | R₆ | R₇ | m.p. ° C.; NMR; Mass |
|---|---|---|---|---|
| II.2 | 2-Cl, 4-OCH₃, 5-CH₃ | —CH₂OCH₃ | 4-F-phenyl | 120 |

TABLE 2-continued

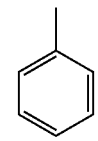

(II)

| COMPOUNDS | $R_1/R_2/R_3$ | $R_6$ | $R_7$ | m.p. ° C.; NMR; Mass |
|---|---|---|---|---|
| II.3 | 2-Cl<br>4-OCH$_3$<br>H | —CH$_2$OCH$_3$ | 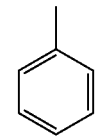 | $^1$H RMN: 7.22-7.42(m, Ar, 6H); 6.95(d, Ar, 1H); 6.78-6.82(m, Ar, 1H); 6.08(s, NH, 1H); 4.57-4.61(m, CH, 1H); 3.80(s, OCH$_3$, 3H); 3.48-3.64(m, OCH$_2$, 2H); 3.35(s, OCH$_3$, 3H); 2.06(s, CH$_3$, 3H). |
| II.4 | 2-Cl<br>4-Cl<br>5-CH$_3$ | —CH$_2$OCH$_3$ | 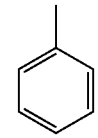 | $^1$H RMN: 7.21-7.44(m, Ar, 7H); 5.91(s, NH, 1H); 4.55-4.59(m, CH, 1H); 3.50-3.67(m, OCH$_2$, 2H); 3.36(s, OCH$_3$, 3H); 2.31(s, CH$_3$, 3H); 2.04(s, CH$_3$, 3H). |
| II.5 | 2-Cl<br>4-OCH$_3$<br>5-CH$_3$ | —CH$_2$OCH$_3$ | 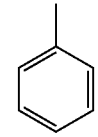 | MS (MH$^+$) 403 $^1$H RMN: 7.24, 7.45(m, Ar, 5H): 7.10(s, Ar, 1H); 6.82(s, Ar, 1H); 5.87(d, NH, 1H); 4.53-4.61(m, CH, 1H); 3.84(s, OCH$_3$, 3H); 3.55-3.68(m, OCH$_2$, 2H); 3.38(s, OCH$_3$, 3H); 2.14(s, CH$_3$, 3H); 2.04(s, CH$_3$, 3H). |
| II.6 | 2-Cl<br>4-Cl<br>H | —CH$_2$OCH$_3$ | 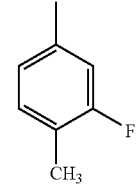 | MS (MH$^+$) 393 $^1$H RMN: 7.19-7.44(m, Ar, 8H); 5.88(d, NH, 1H); 4.59(m, CH, 1H); 3.50-3.67(m, OCH$_2$, 2H); 3.36(s, OCH$_3$, 3H); 2.04(s, CH$_3$, 3H). |
| II.7 | 2-Cl<br>4-OCH$_3$<br>5-CH$_3$ | —CH$_2$OCH$_3$ | 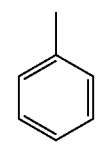 | MS (MH$^+$) 435 $^1$H RMN: 7.06-7.25(m, Ar, 4H); 6.83(s, Ar, 1H); 6.00(m, NH, 1H); 4.52-4.55(m, CH, 1H); 3.81(s, OCH$_3$, 3H); 3.51-3.70(m, OCH$_2$, 2H); 3.35(s, OCH$_3$, 3H); 2.25(s, CH$_3$, 3H); 2.15(s, CH$_3$, 3H); 2.07(s, CH$_3$, 3H). |
| II.8 | 2-Cl<br>4-OCH$_3$<br>H | —(CH$_2$)$_3$CH$_3$ | 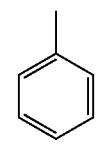 | $^1$H RMN: 7.22-7.37(m, Ar, 6H); 6.96(d, Ar, 1H); 6.78-6.84(dd, Ar, 1H); 5.42-5.45(d, NH, 1H); 4.24-4.34(m, CH, 1H); 3.81(s, OCH$_3$, 3H); 2.06(s, CH$_3$, 3H); 1.79-1.84(m, CH$_2$, 2H); 1.31-1.34(m, CH$_2$CH$_2$, 4H); 0.89(t, CH$_3$, 3H). |
| II.9 | 2-Cl<br>4-OCH$_3$<br>5-CH$_3$ | —(CH$_2$)$_3$CH$_3$ | 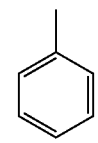 | $^1$H RMN: 7.26-7.46(m, Ar, 5H); 7.11(s, Ar, 1H); 6.84(s, Ar, 1H); 5.52(s, NH, 1H); 4.23-4.32(m, CH, 1H); 3.83(s, OCH$_3$, 3H); 2.15(s, CH$_3$, 3H); 2.07(s, CH$_3$, 3H); 1.80-1.85(m, CH$_2$, 2H); 1.31-1.42(m, CH$_2$CH$_2$, 4H); 0.89(t, CH$_3$, 3H). |
| II.10 | 2-Cl<br>4-OCH$_3$<br>5-CH$_3$ | —(CH$_2$)$_2$CH$_3$ | | $^1$H RMN: 7.24-7.37(m, Ar, 5H); 7.09(s, Ar, 1H); 6.84(s, Ar, 1H); 5.60(s, NH, 1H); 4.20-4.30(m, CH, 1H); 3.82(s, OCH$_3$, 3H); 2.14(s, CH$_3$, 3H); 2.05(s, CH$_3$, 3H); 1.74-2.00(m, CH$_2$, 2H); 1.24-1.48(m, CH$_2$, 2H); 0.91(t, CH$_3$, 3H). |

TABLE 2-continued (II)

| COMPOUNDS | R₁/R₂/R₃ | R₆ | R₇ | m.p. ° C.; NMR; Mass |
|---|---|---|---|---|
| II.11 | 2-Cl<br>4-OCH₃<br>H | —(CH₂)₂CH₃ | phenyl | $^1$H RMN: 7.21-7.39(m, Ar, 6H); 6.94(d, Ar, 1H); 6.77-6.83(dd, Ar, 1H); 5.84(s, NH, 1H); 4.26-4.29(m, CH, 1H); 3.79(s, OCH₃, 3H); 2.05(s, CH₃, 3H); 1.61-1.90(m, CH₂, 2H); 1.20-1.44(m, CH₂, 2H); 0.90(t, CH₃, 3H). |
| II.12 | 2-Cl<br>4-OCH₃<br>5-CH₃ | —CH₂OCH₃ | 4-Cl-phenyl | $^1$H RMN: 7.25-7.39(m, Ar, 4H); 7.08(s, Ar, 1H); 6.83(s, Ar, 1H); 5.87(s, NH, 1H); 4.55(m, CH, 1H); 3.81(s, OCH₃, 3H); 3.47-3.65(m, OCH₂, 2H); 3.35(s, OCH₃, 3H); 2.14(s, CH₃, 3H); 2.06(s, CH₃, 3H). |
| II.13 | 2-Cl<br>4-OCH₃<br>5-CH₃ | —CH₂OCH₃ | 4-(CH₂OCH₃)-phenyl | MS (MH⁺) 447 $^1$H RMN: 7.30-7.42(m, Ar, 4H); 7.10(s, Ar, 1H); 6.83(s, Ar, 1H); 5.90(m, NH, 1H); 4.57(m, CH, 1H); 4.44(s, OCH₂, 2H); 3.81(s, OCH₃, 3H); 3.56-3.65(m, OCH₂, 2H); 3.40(s, OCH₃, 3H); 3.35(s, OCH₃, 3H); 2.14(s, CH₃, 3H); 2.05(s, CH₃, 3H). |
| II.14 | 2-Cl<br>4-Cl<br>5-CH₃ | —CH₂OCH₃ | 4-(CH₂OCH₃)-phenyl | MS (MH⁺) 551 $^1$H RMN: 7.22-7.33(m, Ar, 6H); 5.90(d, NH, 1H); 4.55-4.62(m, CH, 1H); 4.46(s, OCH₂, 2H); 3.49-3.71(m, OCH₂, 2H); 3.41(s, OCH₃, 3H); 3.36(s, OCH₃, 3H); 3.32(s, CH₃, 3H); 2.06(s, CH₃, 3H). |
| II.15 | 2-Cl<br>4-OCH₃<br>H | —(CH₂)₂CH₃ | 4-(CH₂OCH₃)-phenyl | MS (MH⁺) 431 $^1$H RMN: 7.22-7.32(m, Ar, 5H); 6.96(d, Ar, 1H); 6.81(d, Ar, 1H) 5.51(m, NH, 1H); 4.44(s, OCH₂, 2H); 4.25-4.35(m, CH, 1H); 3.81(s, OCH₃, 3H); 3.41(s, OCH₃, 3H); 2.06(s, CH₃, 3H); 1.68-1.87(m, CH₂, 2H); 1.31-1.42(m, CH₂, 2H); 0.91(t, CH₃, 3H). |
| II.16 | 2-Cl<br>4-OCH₃<br>5-CH₃ | —(CH₂)₃CH₃ | 4-F-phenyl | $^1$H RMN: 7.30-7.36(m, Ar, 2H); 7.16(d, Ar, 1H); 7.02-7.08(m, Ar, 2H); 6.88(s, Ar, 1H); 5.76(d, NH, 1H); 4.28-4.31(m, CH, 1H); 3.86(s, OCH₃, 3H); 2.20(s, CH₃, 3H); 2.11(s, CH₃, 3H); 1.72-1.84(m, CH₂, 2H); 1.27-1.47(m, 2CH₂, 4H); 0.92(t, CH₃, 3H). |
| II.17 | 2-Cl<br>4-OCH₃<br>5-CH₃ | —(CH₂)₃CH₃ | 3-F-4-CH₃-phenyl | $^1$H RMN: 6.96-7.25(m, Ar, 4H); 6.83(s, Ar, 1H); 5.61(s, NH, 1H); 4.22(m, CH, 1H); 3.80(s, OCH₃, 3H); 2.33(s, CH₃, 3H); 2.18(s, CH₃, 3H); 2.06(s, CH₃, 3H); 1.64-1.79(m, CH₂, 2H); 1.18-1.34(m, CH₂—CH₂, 4H); 0.89(t, CH₃, 3H). |

TABLE 2-continued (II)

[Structure: thiazole with H3C at 5-position, S, NH-CH(R7)-R6 at 2-position, 4-position bearing phenyl with R1 (ortho), R2 (para), R3 (meta)]

| COMPOUNDS | R₁/R₂/R₃ | R₆ | R₇ | m.p. °C.; NMR; Mass |
|---|---|---|---|---|
| II.18 | 2-Cl<br>4-OCH₃<br>5-CH₃ | —(CH₂)₂CH₃ | 4-fluorophenyl | ¹H RMN: 6.96-7.33(m, Ar, 5H); 6.83(s, Ar, 1H); 5.52(d, NH, 1H); 4.22-4.32(m, CH, 1H); 3.81(s, OCH₃, 3H); 2.15(s, CH₃, 3H); 2.06(s, CH₃, 3H); 1.59-1.84(m, CH₂, 2H); 1.18-1.46(m, CH₂, 2H); 0.90(t, CH₃, 3H). |
| II.19 | 2-Cl<br>4-OCH₃<br>H | —(CH₂)₂CH₃ | 4-fluorophenyl | ¹H RMN: 6.77-7.34(m, Ar, 7H); 5.53(d, NH, 1H); 4.23-4.33(m, CH, 1H); 3.80(s, OCH₃, 3H); 2.06(s, CH₃, 3H); 1.59-1.88(m, CH₂, 2H); 1.17-1.46(m, CH₂, 2H); 0.90(t, CH₃, 3H). |
| II.20 | 2-Cl<br>4-OCH₃<br>5-CH₃ | cyclobutyl | cyclobutyl | ¹H RMN: 7.16(s, Ar, 1H); 6.86(s, Ar, 1H); 4.84(d, NH, 1H); 3.83(s, OCH₃, 3H); 3.14-3.22(m, CH, 1H); 2.13-2.39(m, CHx2, 2H); 2.17(s, CH₃, 3H); 2.13(s, CH₃, 3H); 1.67-1.94(m, CH₂x6, 12H). |
| II.21 | 2-Cl<br>4-OCH₃<br>5-CH₃ | cyclobutyl | 4-fluorophenyl | ¹H RMN: 7.22-7.33(m, Ar, 2H); 7.10(s, Ar, 1H); 6.93-7.05(m, Ar, 2H); 6.81(s, Ar, 1H); 5.62(d, NH, 1H); 4.10-4.16(m, CH, 1H); 3.81(s, OCH₃, 3H); 2.37-2.53(m, CH, 1H); 2.15(s, CH₃, 3H); 2.06(s, CH₃, 3H); 1.75-1.93(m, 3CH₂, 6H). |
| II.22 | 2-Cl<br>4-OCH₃<br>5-CH₃ | —(CH₂)₂-cyclopropyl | 4-fluorophenyl | ¹H RMN: 7.25-7.39(m, Ar, 2H); 7.10(s, Ar, 1H); 6.95-7.08(m, Ar, 2H); 6.82(s, Ar, 1H); 6.22(m, NH, 1H); 4.25-4.35(m, CH, 1H); 3.81(s, OCH₃, 3H); 2.15(s, CH₃, 3H); 2.07(s, CH₃, 3H); 1.75-2.00(m, CH₂, 2H); 1.15-1.35(m, CH₂, 2H).; 0.56-0.75(m, CH cyclopropyle, 1H); 0.36-0.48(m, CH₂ cyclopropyle, 2H).; −0.03-0.05(m, CH₂ cyclopropyle, 2H). |

PREPARATION OF THE N-SUBSTITUTED THIAZOLES COMPOUNDS I

Example 1

[4-(2-Chloro-4-methoxy-5-methylphenyl)-5-methylthiazol-2-yl]-[1-(4-fluorophenyl)-2-methoxyethyl) prop-2-ynylamine Compound I.1

50 mg of 60% sodium hydride in oil are added, with stirring and at 0° C., to 500 mg (1.2 mmol) of Compound II.2 in 6 ml of anhydrous dimethylformamide. The reaction mixture is stirred for twenty minutes at 0° C., followed by addition of 0.22 ml (2 mmol) of an 80% solution of propargyl bromide in toluene. The reaction mixture is stirred for one hour at 10° C., followed by addition of 0.5 ml of ethanol and then 10 ml of water. The mixture is extracted with twice 50 ml of ethyl acetate. The organic phase is washed with water and then with saturated aqueous sodium chloride solution, dried over anhydrous sodium sulphate and then evaporated to dryness. The crude residue is chromatographed on a column of silica gel [eluent: 9/1 (v/v) cyclohexane/ethyl acetate]. 400 mg of the pure expected compound are obtained. Yield=73%, hydrochloride hemihydrate: m.p.=94° C.

The following products described in Table 3 were prepared in the same way:

TABLE 3

General structure: 5-methyl-thiazole with 4-aryl substituent (bearing R1, R2, R3) and 2-N(propargyl)(CHR6-R7) amino group.

| # | R1/R2/R3 | R6 | R7 | Mass; m.p. °C. (HCl) |
|---|---|---|---|---|
| 2 | 2-Cl, 4-OCH₃, H | —CH₂OCH₃ | phenyl | 70 |
| 3 | 2-Cl, 4-Cl, 5-CH₃ | —CH₂OCH₃ | phenyl | MS (MH⁺) 445; 74 |
| 4 | 2-Cl, 4-OCH₃, 5-CH₃ | —CH₂OCH₃ | phenyl | MS (MH⁺) 441; 68 |
| 5 | 2-Cl, 4-Cl, H | —CH₂OCH₃ | phenyl | MS (MH⁺) 431; 80 |
| 6 | 2-Cl, 4-OCH₃, 5-CH₃ | —CH₂OCH₃ | 3-fluoro-4-methylphenyl | MS (MH⁺) 473; 82 |
| 7 | 2-Cl, 4-OCH₃, H | —(CH₂)₃CH₃ | phenyl | MS (MH⁺) 439; 71 |
| 8 | 2-Cl, 4-OCH₃, 5-CH₃ | —(CH₂)₃CH₃ | phenyl | MS (MH⁺) 453; 79 |
| 9 | 2-Cl, 4-OCH₃, 5-CH₃ | —(CH₂)₂CH₃ | phenyl | MS (MH⁺) 439; 69 |
| 10 | 2-Cl, 4-OCH₃, H | —(CH₂)₂CH₃ | phenyl | MS (MH⁺) 425; 100 |
| 11 | 2-Cl, 4-OCH₃, 5-CH₃ | —CH₂OCH₃ | 4-chlorophenyl | MS (MH⁺) 475; 58 |
| 12 | 2-Cl, 4-OCH₃, 5-CH₃ | —CH₂OCH₃ | 4-(CH₂OCH₃)phenyl | MS (MH⁺) 485; 71 |
| 13 | 2-Cl, 4-Cl, 5-CH₃ | —CH₂OCH₃ | 4-(CH₂OCH₃)phenyl | MS (MH⁺) 489; 92 |
| 14 | 2-Cl, 4-OCH₃, 5-CH₃ | —(CH₂)₂CH₃ | 4-(CH₂OCH₃)phenyl | MS (MH⁺) 483; 93 |
| 15 | 2-Cl, 4-OCH₃, H | —(CH₂)₂CH₃ | 4-(CH₂OCH₃)phenyl | MS (MH⁺) 469; 66 |

TABLE 3-continued

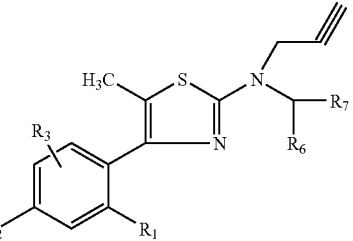

| R₁/R₂/R₃ | R₆ | R₇ | Mass; m.p. ° C. (HCl) |
|---|---|---|---|
| 16 | 2-Cl<br>4-OCH₃<br>5-CH₃ | —(CH₂)₃CH₃ |  | MS (MH⁺) 471; 61 |
| 17 | 2-Cl<br>4-OCH₃<br>5-CH₃ | —(CH₂)₃CH₃ | 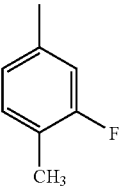 | MS (MH⁺) 485; 69 |
| 18 | 2-Cl<br>4-OCH₃<br>5-CH₃ | —(CH₂)₂CH₃ |  | MS (MH⁺) 457; 85 |
| 19 | 2-Cl<br>4-OCH₃<br>H | —(CH₂)₂CH₃ |  | MS (MH⁺) 443; 83 |
| 20 | 2-Cl<br>4-OCH₃<br>5-CH₃ | 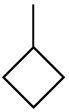 | 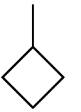 | MS (MH⁺) 429; 83 |
| 21 | 2-Cl<br>4-OCH₃<br>5-CH₃ | 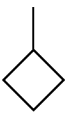 |  | MS (MH⁺) 469; 106 |
| 22 | 2-Cl<br>4-OCH₃<br>5-CH₃ | 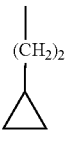 |  | MS (MH⁺) 483; 78 |

Example 23

Allyl-[4-(2-chloro-4-methoxyphenyl)-5-methylthiazol-2-yl]-(2-methoxy-1-phenylethyl)amine A solution of 1.95 g (5 mmol) of aminothiazole (Compound II.3) in 25 ml of dimethylformamide is stirred at 0° C. and 320 mg (8 mmol) of sodium hydride (at 60% in oil) are added. After stirring for 20 minutes at 0° C., 0.86 ml (10 mmol) of allyl bromide is added. The reaction mixture is stirred at room temperature for one hour, followed by successive addition of 2 ml of ethanol and 50 ml of water. The mixture is extracted with 200 ml of ethyl acetate and the organic phase is washed with water and then with saturated sodium chloride solution, dried over anhydrous sodium sulphate and then evaporated to dryness. The crude residue obtained is chromatographed on a column of silica gel, eluting with 9/1 (v/v) cyclohexane/ethyl acetate. 1.25 g (2.7 mmol) of pure product are obtained. Yield=54%; MS (MH⁺) 429; hydrochloride monohydrate; m.p.=70° C.

Example 24

But-2-ynyl-[4-(2-chloro-4-methoxyphenyl)-5-methylthiazol-2-yl]-[2-methoxy-1-phenylethyl]amine A solution of 2.8 g (7.17 mmol) of aminothiazole (Compound II.3) in 35 ml of dimethylformamide is stirred at 0° C. and 400 mg (10 mmol) of sodium hydride (at 60% in oil) are added. After stirring for twenty minutes at 0° C., 1.33 g (10 mmol) of 2-bromobutyne (Ferchan) are added. The reaction mixture is stirred at room temperature for one hour, followed by successive addition of 2 ml of ethanol and 50 ml of water. The mixture is extracted with 200 ml of ethyl acetate; the organic phase is washed with water and then with saturated sodium chloride solution, dried over anhydrous sodium sulphate and then evaporated to dryness. The residue obtained is purified by chromatography on a column of silica gel, eluting with 15/1 (v/v) cyclohexane/ethyl acetate. 2.34 g of pure product are obtained. Yield=74%; MS (MH+) 441; hydrochloride hemihydrate; m.p.=70° C.

PREPARATION OF THE AMINES IN THE FORM OF AN ENANTIOMER

Compound VI'

First Method a) (R)-2-Amino-2-(4-fluorophenyl)ethanol Compound 1'.1

240 ml (240 mmol) of a 1M solution of lithium aluminium hydride in tetrahydrofuran are stirred at reflux, followed by portionwise addition of 20 g (118 mmol) of (R)-(4-fluorophenyl)glycine. After stirring at reflux for six hours thirty minutes, the reaction mixture is stirred at 0° C., followed by slow addition of 9.5 ml of water, 9.5 ml of 15% sodium hydroxide solution and then 28.5 ml of water. The suspension obtained is filtered through Celite. The filtrated is concentrated and taken up in 1 liter of dichloromethane. The solution is washed with saturated sodium chloride solution, dried over anhydrous sodium sulphate and then evaporated to dryness. A crystallization from isopropyl ether gives 13.22 g (85.2 mmol) of crystalline product. Yield=72%, m.p.=95° C.; MS (MH⁺): 156.

¹H NMR (DMSO-d₆): 7.30-7.41 (m, Ar, AH); 7.01-7.13 (m, Ar, 2H); 4.73 (s, OH, 1H); 3.84 (m, CH, 1H); 3.35-3.45 (m, CH₂O, 2H); 1.82 (s, NH₂, 2H).

b) (R)-1-(4-Fluorophenyl)-2-methoxyethylamine Compound VI'.1

3.64 g (91 mmol) of potassium hydride, obtained by washing 8.1 g of an oily suspension with pentane, are suspended in 70 ml of tetrahydrofuran and stirred at 10° C. A solution of 13.22 g (85 mmol) of Compound 1'.1 in 175 ml of tetrahydrofuran is added slowly. After stirring for sixteen hours at room temperature, a solution of 5.2 ml (83.5 mmol) of iodomethane in 105 ml of tetrahydrofuran is added over two hours. The reaction mixture is stirred for three hours at room temperature and is then poured into 1 liter of ice-cold water containing salt. The mixture is extracted with 1 liter of tert-butyl methyl ether. The organic phase is washed with water than then with saturated sodium chloride solution, dried over anhydrous sodium sulphate and then evaporated to dryness. 11.87 g (70 mmol) of oily amine are obtained.

Yield=82%.

$^1$H NMR: 7.24-7.38 (m, Ar, 2H); 6.93-7.05 (m, Ar, 2H); 4.16 (m, CH, 1H); 3.45 (dd, CH$_2$, 1H); 3.36 (s, OCH$_3$, 3H); 3.29 (d, CH$_2$, 1H) 1.66 (s, NH$_2$, 2H).

The following compound is obtained in the same way, starting with (R)-phenylglycine:

(R)-2-Methoxy-1-phenylethylamine Compound VI'.2

Second Method a) (S)-2-Amino-3-methyl-1,1-diphenylbutan-1-ol Compound 2'.1

A solution of 600 ml of 3.0 M phenylmagnesium bromide (1790 mmol) in diethyl ether is stirred at 0° C. and diluted with 300 ml of THF, followed by portionwise addition of 50 g (298 mmol) of L-valine methyl ester hydrochloride while keeping the temperature below 10° C. After stirring for three hours at room temperature, the reaction mixture is poured slowly into ice-cold ammonium chloride solution. 500 ml of diethyl ether and 500 ml of ethyl acetate are added to the mixture, followed by stirring overnight at room temperature. After separation of the phases by settling, the aqueous phase is re-extracted with 1 L of TBME (tert-butyl methyl ether). The combined organic phases are stirred at 0° C. and are acidified slowly with about 40 ml of 35% hydrochloric acid in water. The hydrochloride precipitate thus formed is filtered off and rinsed with TBME. The mixture is then taken up in 1 L of dichloromethane and 1 L of water and is basified at 0° C. with about 50 ml of 35% caustic soda. After separation of the phases by settling, the aqueous phase is re-extracted with 1 L of dichloromethane. The combined organic phases are washed with water and then with brine, dried over sodium sulphate and concentrated. After crystallization from isopropyl ether, 61 g of Compound 2'.1 are obtained (yield=87%)

$[\alpha D]_D^{25}=-127.8°$ (CHCl$_3$ c=0.639)

$^1$H NMR: 7.00-7.60 (Ar, m, 10H); 5.24 (—OH, s, 1H); 3.66 (—CH—N, d, J=1.5, 1H); 1.53 (—CH—, hept d, J=1.5 and 7, 1H); 1.16 (—NH$_2$, s, 2H); 0.81 (—CH$_3$, 2d, J=7, 6H).

The following product is obtained in a similar manner, starting with D-valine methyl ester hydrochloride:

(R)-2-Amino-3-methyl-1,1-diphenylbutan-1-ol Compound 2'.2

These compounds are used as chiral auxiliaries in the enantioselective reduction of the O-benzyl oximes 6'.

b) Synthesis of the Substituted Phenyl Ketones. Compounds 3'

Procedure A

2-Cyclopropyl-1-(3-fluoro-4-methylphenyl)ethan-1-one Compound 3'.1

50 ml of diethyl ether and one crystal of iodine are added to 10.2 g (418 mmol) of magnesium turnings and the mixture is stirred at room temperature. A solution of 75.53 g (398 mmol) of 4-bromo-2-fluorotoluene in 370 ml of diethyl ether is added over three hours so as to maintain a moderate reflux. The reaction mixture is then refluxed for one hour thirty minutes, after which it is cooled and filtered through glass wool. The solution obtained is added slowly to a solution of 32.3 g (398 mmol) of cyclopropylacetonitrile in 230 ml of diethyl ether stirred at 0° C. The reaction mixture is stirred overnight at room temperature. It is then stirred at 0° C. and 200 ml of 2N hydrochloric acid are added slowly. After separation of the ether phase, the acidic aqueous phase is extracted with ethyl acetate. The combined organic phases are washed with water and then with saturated sodium chloride solution, dried over anhydrous sodium sulphate and then evaporated to dryness. The crude extract is purified by chromatography on silica gel (elution solvent: 20/1 cyclohexane/ethyl acetate). 53.3 g of ketone 3'-1 are obtained (yield=70%).

$^1$H NMR: 7.54-7.64 (m, 2H, Ar); 7.22-7.30 (m, 1H, Ar); 2.82 (d, J=6.7 Hz, 2H, CH$_2$); 2.31 (s, 3H, CH$_3$); 1.07-1.20 (m, 1H, CH cyclopropyl); 0.55-0.65 (m, 2H, CH$_2$ cyclopropyl); 0.15-0.21 (m, 2H, CH$_2$ cyclopropyl).

The following ketones were synthesized by the same process:

1-(4-Ethylphenyl)-2-methoxyethan-1-one Compound 3'.2
2-Cyclopropyl-1-(4-methylphenyl)ethan-1-one Compound 3'.3
2-Cyclopropyl-1-(4-fluorophenyl)ethan-1-one Compound 3'.4

Procedure B

Method described for Compound 3.5 (reaction of a phenyllithium reagent with a Weinreb amide):

2-Methoxy-1-(3,4-methylenedioxyphenyl)ethan-1-one Compound 3'.5
1-(4-Methoxymethylphenyl)pentan-1-one Compound 3'.6
1-(3-Fluoro-4-methylphenyl)butan-1-one Compound 3'.7
1-(3-Fluoro-4-methylphenyl)pentan-1-one Compound 3'.8
1-(3-Fluoro-4-methoxymethylphenyl)butan-1-one Compound 3'.9
2-Cyclopropyl-1-(3,4-methylenedioxyphenyl)ethan-1-one Compound 3'.10
1-(3,4-Methylenedioxyphenyl)ethan-1-one Compound 3'.11 c) Synthesis of the O-benzyl Oximes. Compounds 6'

The O-benzyl oximes are prepared by O-benzylation of the corresponding oximes according to the process which follows (the starting oximes are obtained from ketones by one of the two synthetic methods described previously for Compound 4.1).

1-(3-Fluoro-4-methylphenyl)-2-methoxyethan-1-one O-benzyloxime Z isomer Compound 6'.1

A solution of 42.5 g (217 mmol) of 1-(3-fluoro-4-methylphenyl)-2-methoxyethan-1-one oxime Z (Compound 4.1) in 100 ml of dimethylformamide is stirred at 0° C. and 15.6 g (325 mmol, 1.5 eq.) of sodium hydride at 50% in oil are added portionwise. The reaction mixture is stirred for fifteen minutes, followed by slow addition of a solution containing 30 ml (280 mmol, 1.3 eq.) of benzyl bromide in 100 ml of dimethylformamide. The reaction mixture is stirred for two hours at room temperature, followed by cooling to 0° C. and addition of 5 ml of ethanol and then 50 ml of water. The resulting mixture is extracted with ethyl acetate. The organic phase is washed with water and then with saturated sodium chloride solution. It is then dried over sodium sulphate and evaporated to dryness. The oil thus obtained is purified by chromatography on silica gel (eluent: 7/3 (v/v) cyclohexane/dichloromethane). 39 g of Compound 6'.1 (Z) are obtained; yield=63%.

$^1$H NMR: 7.10-7.50 (Ar, m, 8H); 5.22 (—O—CH$_2$-Ph, s, 2H); 4.58 (—CH$_2$—O, s, 2H); 3.28 (OCH$_3$, s, 3H); 2.26 (CH$_3$-Ph, d, J=1.8, 3H).

The following compounds are prepared in the same way:
- 1-(4-Chloro-3-fluorophenyl)-2-methoxyethan-1-one O-benzyloxime (Z) Compound 6'.2
- 1-(4-Chlorophenyl)-2-methoxyethan-1-one O-benzyloxime (Z) Compound 6'.3
- 2-Methoxy-1-(3,4-methylenedioxyphenyl)ethan-1-one O-benzyloxime (Z) Compound 6'.4
- 1-(4-Ethylphenyl)-2-methoxyethan-1-one O-benzyloxime (Z) Compound 6'.5
- 2-Methoxy-1-(4-methoxymethylphenyl)ethan-1-one O-benzyloxime (Z) Compound 6'.6
- 1-Phenylbutan-1-one O-benzyloxime (E) Compound 6'.7
- 1-(4-Methoxymethylphenyl)butan-1-one O-benzyloxime (E) Compound 6'.8
- 1-(4-Methoxymethylphenyl)pentan-1-one O-benzyloxime (E) Compound 6'.9
- 2-Cyclopropyl-1-phenylethan-1-one O-benzyloxime (E) Compound 6'.10
- 2-Cyclopropyl-1-(4-fluorophenyl)ethan-1-one O-benzyloxime (E) Compound 6'.11
- 1-(4-Fluorophenyl)pentan-1-one O-benzyloxime (E) Compound 6'.12
- Cyclopropylphenyl ketone O-benzyloxime (E) Compound 6'.13
- 1-(3-Fluoro-4-methylphenyl)butan-1-one O-benzyloxime (E) Compound 6'.14
- 1-(3-Fluoro-4-methylphenyl)pentan-1-one O-benzyloxime (E) Compound 6'.15
- 2-Cyclopropyl-1-(3-fluoro-4-methylphenyl)ethan-1-one O-benzyloxime (E) Compound 6'.16
- 1-(4-Fluorophenyl)butan-1-one O-benzyloxime (E) Compound 6'.17
- 1-(3-Fluoro-4-methoxymethylphenyl)butan-1-one O-benzyloxime (E) Compound 6'.18
- 2-Cyclopropyl-1-(4-chlorophenyl)ethan-1-one O-benzyloxime (E) Compound 6'.19
- 2-Cyclopropyl-1-(4-methylphenyl)ethan-1-one O-benzyloxime (E) Compound 6'.20
- 2-Cyclopropyl-1-(4-fluorophenyl)ethan-1-one O-benzyloxime (E) Compound 6'.21
- 2-Cyclopropyl-1-(4-bromophenyl)ethan-1-one O-benzyloxime (E) Compound 6'.22
- 2-Cyclopropyl-1-(3,4-methylenedioxyphenyl)ethan-1-one O-benzyloxime (E) Compound 6'.23
- 1-(3,4-Methylenedioxyphenyl)butan-1-one O-benzyloxime (E) Compound 6'.24 d) Synthesis of the Enantiomeric Amines (R)-1-(3-Fluoro-4-methylphenyl)-2-methoxyethylamine Compound VI'.3

A solution of 86.5 g of Compound 2'.1 (330 mmol) in 600 ml of tetrahydrofuran is stirred at a temperature below 30° C., followed by slow addition of 670 ml of a 1M borane-tetrahydrofuran solution (670 mmol). The temperature is allowed to rise to room temperature over two hours. The reaction medium is then stirred at 0° C. and 39 g (132 mmol) of Compound 6'.1 predissolved in 100 ml of tetrahydrofuran are added. After stirring for twenty hours at room temperature, the reaction mixture is cooled to 0° C. and 1 liter of 2N hydrochloric acid is added. This mixture is left stirring for sixteen hours. The mixture is basified at 0° C. by addition of 35% sodium hydroxide, followed by extraction with ethyl acetate. This extract is washed with water and with saturated aqueous sodium chloride solution, and then dried over sodium sulphate and evaporated to dryness. The residue obtained is chromatographed on a column of silica gel (eluent: 95/5 (v/v) dichloromethane/methanol). 17 g of Compound VI'.3 are obtained; yield=79%.

$^1$H NMR: 6.90-7.20 (m, Ar, 3H); 4.14 (dd, J$_1$=4 Hz, J$_2$=8.5 Hz, CHN, 1H); 3.47 (dd, J$_1$=4 Hz, J$_2$=9 Hz, —CH$_2$—O, 1H); 3.37 (s, OCH$_3$, 3H); 3.32 (dd, J$_1$=8.5 Hz, J$_2$=9 Hz, —CH$_2$—O, 1H); 2.24 (d, J=1.8 Hz, CH$_3$-Ph, 3H), 1.68 (s, —NH$_2$, 2H).

Chiral HPLC: % enantiomers: Yield=99.5% S=0.5% ee=99.0%

General Comments:

The enantiomeric excesses (ee) are evaluated from the chromatograms (HPLC or chiral SFC) of these amines or of the corresponding thioureas IV'

The following are obtained in the same way:
- (R)-1-(4-chloro-3-fluorophenyl)-2-methoxyethylamine Compound VI'.4 ee=98.2%
- (R)-1-(4-chlorophenyl)-2-methoxyethylamine Compound VI'.5 ee=98.6%
- (R)-2-methoxy-1-(3,4-methylenedioxyphenyl)ethylamine Compound VI'.6 ee>99%
- (R)-1-(4-ethylphenyl)-2-methoxyethylamine Compound VI'.7 ee>99%
- (R)-2-methoxy-1-(4-methoxymethylphenyl)ethylamine Compound VI'.8 ee>99%
- (S)-(1-phenyl)butylamine Compound VI'.9 ee=97.1%
- (S)-1(4-methoxymethylphenyl)butylamine Compound VI'.10 ee=97.1%
- (S)-1-(4-methoxymethylphenyl)pentylamine Compound VI'.11 ee=96.8%
- (S)-2-cyclopropyl-1-phenylethylamine Compound VI'.12 ee=95.8%
- (S)-2-cyclopropyl-1-(4-fluorophenyl)ethylamine Compound VI'.13 ee=95.4%
- (S)-1-(4-fluorophenyl)pentylamine Compound VI'.14
- (S)-cyclopropylphenylmethylamine Compound VI'.15 ee=90%
- (S)-1-(3-fluoro-4-methylphenyl)butylamine Compound VI'.16 ee>99%
- (S)-1-(3-fluoro-4-methylphenyl)pentylamine Compound VI'.17 ee=97%
- (S)-2-cyclopropyl-1-(3-fluoro-4-methylphenyl)ethylamine Compound VI'.18 ee>99%
- (S)-1-(4-fluorophenyl)butylamine Compound VI'.19 ee=98.4%
- (S)-1-(3-fluoro-4-methoxymethylphenyl)butylamine Compound VI'.20 ee=90.5%
- (S)-2-cyclopropyl-1-(4-chlorophenyl)ethylamine Compound VI'.21 ee>99%
- (S)-2-cyclopropyl-1-(4-methylphenyl)ethylamine Compound VI'.22 ee=85.6%
- (S)-2-cyclopropyl-1-(4-fluorophenyl)ethylamine Compound VI'.23 ee=98.5%
- (S)-2-cyclopropyl-1-(4-bromophenyl)ethylamine Compound VI'.24 ee=98.3%
- (S)-2-cyclopropyl-1-(3,4-methylenedioxyphenyl)ethylamine Compound VI'.25 ee=96.7%
- (S)-1-(3,4-methylenedioxyphenyl)butylamine Compound VI'.26 ee=84%

Third Method

To improve the enantiomeric excess, the above amines can be treated with organic acids in the form of pure enantiomers (for example N-acetyl-L-leucine) and recrystallization:

(S)-(1-phenyl)butylamine Compound VI'.9

Salification with N-acetyl-L-leucine:

A solution of 10.4 g (60 mmol) of N-acetyl-L-leucine in 70 ml of anhydrous methanol is stirred at 60° C., followed by dropwise addition of a solution of 9.0 g (60 mmol) of (S)-(1-phenyl)butylamine Compound VI'.9 (ee=97.1%) in 30 ml of anhydrous methanol. At the end of the addition, the methanolic solution is brought to the boiling point (total dissolution) and left to stand overnight. After filtration and rinsing with 20 ml of cold anhydrous methanol, 7.7 g of crystals are recovered which are dissolved in a minimum of water. After basification with 1N sodium hydroxide and extraction with dichloromethane, the organic phase is washed with saturated sodium chloride solution, dried over sodium sulphate and evaporated under vacuum. 3.4 g of amine are obtained in the form of an oil.

$^1$H NMR: 7.16-7.36 (m, Ar, 5H); 3.87 (m, —CH—N, 1H); 1.57-1.69 (m, —CH—CH$_2$, 2H); 1.47 (s, NH$_2$, 2H); 1.15-1.40 (m, —CH$_2$CH$_3$, 2H); 0.88 (t, —CH$_2$CH$_3$, 3H).

Chiral HPLC: % enantiomers: S=100% Yield=0% ee=100%

$[\alpha]_D^{25}$=−22.0° (c=1.05, CHCl$_3$)

PREPARATION OF THE THIOUREAS IN THE FORM OF AN ENANTIOMER

Compound IV'

First Method

N[(R)-1-(4-fluorophenyl)-2-methoxyethyl]thiourea Compound IV'.1

4.23 ml (36.6 mmol) of benzoyl chloride are added, at 0° C., to a stirred solution of 2.83 g (37.2 mmol) of ammonium isothiocyanate in 75 ml of acetone. After thirty minutes, 6 g (35.5 mmol) of Compound VI'.1 dissolved in 75 ml of acetone are added slowly. The reaction mixture is stirred for two hours at room temperature and then concentrated under reduced pressure. The suspension is taken up in 200 ml of tert-butyl methyl ether and 200 ml of water. The organic phase is washed with water and then with saturated sodium chloride solution, dried over anhydrous sodium sulphate and then evaporated to dryness. The evaporation residue is dissolved in 180 ml of ethanol and 3.75 ml (75 mol) of hydrazine monohydrate are added to the solution obtained. After stirring for twenty-four hours at room temperature, the reaction mixture is evaporated. The evaporation residue is dissolved in 200 ml of ethyl acetate and the organic phase is washed with water and then with saturated sodium chloride solution, dried over anhydrous sodium sulphate and evaporated to dryness. The evaporation residue is chromatographed on a column of silica gel, eluting with 1/1 (v/v) cyclohexane/ethyl acetate. 5 g (23 mmol) of a solid white product are obtained;
yield=63%; m.p.=119° C.

$^1$H NMR (DMSO-d$_6$): 8.10 (d, NH, 1H); 7.28-7.32 (m, Ar, 2H); 7.08-7.17 (m, Ar and NH$_2$, 4H); 5.45 (m, CH—N, 1H); 3.54-3.62 (m, CH—CH$_2$, 2H); 3.24 (s, OCH$_3$, 3H).

$[\alpha]_D^{19}$=+32.0° (c=0.87 CH$_2$Cl$_2$).

Supercritical chiral chromatography ee=100%

The following products are obtained in the same way:
N—[(R)-2-methoxy-1-phenylethyl]thiourea Compound IV'.2
m.p.=140° C. $[\alpha]_D^{19}$=+4.6° (c=1.0 CH$_2$Cl$_2$).
N—[(R)-1-(4-chlorophenyl)-2-methoxyethyl]thiourea Compound IV'.3
m.p.=133° C. $[\alpha]_D^{19}$=+25.7° (c=1.04 CH$_2$Cl$_2$).
N—[(R)-2-methoxy-1-(3,4-methylenedioxyphenyl)ethyl] thiourea Compound IV'.4
m.p.=160° C. $[\alpha]_D^{19}$=+19.4° (c=0.68 CH$_2$Cl$_2$).
N—[(R)-1-(4-ethylphenyl)-2-methoxyethyl]thiourea Compound IV'.5
m.p.=116° C. $[\alpha]_D^{19}$=+20.0° (c=0.93 CH$_2$Cl$_2$).
N—[(S)-1-phenylbutyl]thiourea Compound IV'.6
m.p.=140° C. $[\alpha]_D^{19}$=+48.7° (c=0.82 CH$_2$Cl$_2$).
N—[(R)-2-methoxy-1-(4-methoxymethylphenyl)ethyl] thiourea Compound IV'.7

$^1$H NMR: 7.25-7.36 (m, Ar, 4H); 6.85 (m, NH, 1H); 5.93 (m, NH$_2$, 2H); 4.78 (m, CH—N, 1H); 4.43 (s, O—CH$_2$, 2H); 3.58-3.65 (m, O—CH$_2$, 2H); 3.38 (s, OCH$_3$, 3H); 3.35 (s, O—CH$_3$, 3H).

$[\alpha]_D^{19}$=+20.5° (c=0.95 CH$_2$Cl$_2$).
N—[(S)-1-(4-methoxymethylphenyl)pentyl]thiourea Compound IV'.8

$^1$H NMR: 7.22-7.35 (m, Ar, 4H); 6.71 (m, NH, 1H); 5.63 (m, NH$_2$, 2H); 4.42 (s, O—CH$_2$, 2H); 4.40 (m, CH, 1H); 3.39 (s, OCH$_3$, 3H); 1.68-1.79 (m, CH$_2$, 2H); 1.14-1.30 (m, CH$_2$—CH$_2$, 4H); 0.81-0.87 (m, CH$_3$, 3H).

$[\alpha]_D^{19}$=+49.8° (c=1.04 CH$_2$Cl$_2$).
N—[(S)-1-(4-methoxymethylphenyl)butyl]thiourea Compound IV'.9

$^1$H NMR: 7.20-7.40 (m, Ar, 4H); 6.69 (m, NH, 1H); 5.63 (m, NH$_2$, 2H); 4.41 (s, O—CH$_2$, 2H); 4.40 (m, CH, 1H); 3.39 (s, OCH$_3$, 3H); 1.59-1.88 (m, CH—CH$_2$—CH$_2$, 2H); 1.15-1.44 (m, CH$_2$—CH$_2$—CH$_3$, 2H); 0.85-0.92 (m, CH$_2$—CH$_3$, 3H).

$[\alpha]_D^{19}$=+43.9° (c=1.17 CH$_2$Cl$_2$).
N—[(S)-2-cyclopropyl-1-phenylethyl]thiourea Compound IV'.10
m.p.=80° C. $[\alpha]_D^{19}$=+55.0° (c=0.97 CH$_2$Cl$_2$).
ee=95.8%
N—[(R)-1-(3-fluoro-4-methylphenyl)-2-methoxyethyl] thiourea Compound IV'.11
m.p.=149° C. $[\alpha]_D^{20}$=+30.3° (c=0.97 CH$_2$Cl$_2$).
N—[(R)-1-(3-fluoro-4-chlorophenyl)-2-methoxyethyl] thiourea Compound IV'.12
m.p.=110° C. $[\alpha]_D^{20}$=+29.1° (c=1.04 CH$_2$Cl$_2$).
N—[(S)-1-(4-fluorophenyl)pentyl]thiourea Compound IV'.13
m.p.=118° C. $[\alpha]_D^{20}$=−19.2° (c=0.78 methanol)
N—[(S)-cyclopropylphenylmethyl]thiourea Compound IV'.14

$^1$H NMR: 7.25-7.41 (m, Ar, 5H); 6.92 (m, NH, 1H); 5.58 (m, NH$_2$, 2H); 3.92 (m, CH, 1H); 1.08-1.25 (m, CH, cyclopropyl, 1H); 0.35-0.69 (m, 2CH$_2$ cyclopropyl, 4H).

$[\alpha]_D^{20}$=+33.5° (c=0.48 methanol); ee=90%
N—[(S)-1-(3-fluoro-4-methylphenyl)butyl]thiourea Compound IV'.15
m.p.=129° C. $[\alpha]_D^{20}$=44.4° (c=0.81 CH$_2$Cl$_2$);
ee=99%
N—[(S)-1-(3-fluoro-4-methylphenyl)pentyl]thiourea Compound IV'.16
m.p.=124° C. $[\alpha]_D^{20}$=+4.6° (c=1.4 CH$_2$Cl$_2$);
ee=97%
N—[(S)-2-cyclopropyl-1-(3-fluoro-4-methylphenyl) ethyl]thiourea Compound IV'.17
m.p.=91° C. $[\alpha]_D^{22}$=+55.4° (cp=0.9 CH$_2$Cl$_2$);
ee=99%
N—[(S)-1(4-fluorophenyl)butyl]thiourea Compound IV'.18

$^1$H NMR: 7.21-7.28 (m, Ar, 2H); 6.99-7.09 (m, Ar, 2H); 6.75 (s, NH, 1H); 5.71 (s, NH$_2$, 2H); 4.35-4.60 (m, CH, 1H); 1.65-1.85 (m, CH$_2$, 2H); 1.18-1.45 (m, CH$_2$, 2H) 0.86-0.93 (m, CH$_3$, 3H).

$[\alpha]_D^{22}=+49°$ (c=0.95 CH$_2$Cl$_2$); ee=98.4%.
N—[(S)-2-cyclopropyl-1-(4-chlorophenyl)ethyl]thiourea Compound IV'.19
m.p.=93.7° C. $[\alpha]_D^{23}=+53°$ (c=0.5 CH$_2$Cl$_2$); ee=99.1%.
N—[(S)-2-cyclobutyl-1-(4-fluorophenyl)ethyl]thiourea Compound IV'.20
m.p.=104° C. $[\alpha]_D^{20}=-21°$ (c=1 methanol); ee=98.5%
N—[(S)-2-cyclopropyl-1-(4-bromophenyl)ethyl]thiourea Compound IV'.21
m.p.=130° C. $[\alpha]_D^{20}=+57°$ (c=0.67 CH$_2$Cl$_2$); ee=98.3%.
N—[(S)-2-cyclopropyl-1-(3,4-methylenedioxyphenyl)ethyl]thiourea Compound IV'.22
m.p.=125° C. $[\alpha]_D^{19}=+63°$ (c=0.75 CH$_2$Cl$_2$); ee=96.7%.

Second Method a) Production by Chromatography of Thioureas in Enantiomeric Form (ee>99%) from Thioureas Enriched in One Enantiomer:
N—[(S)-2-cyclopropyl-1-phenylethyl]thiourea Compound IV'.10
Starting with a mixture containing the S enantiomer as the majority product (ee 95.8%), and after separation by chromatography on a Chiracel OJ phase eluting with 97/3 isohexane/ethanol, the pure S enantiomer is obtained (ee 100%)
m.p.=84° $[\alpha]_D^{19}=+59.3°$ (c=1.06 CH$_2$Cl$_2$).
N—[(S)-2-cyclopropyl-1-(4-fluorophenyl)ethyl]thiourea Compound IV'.23
m.p.=105° $[\alpha]_D^{22}=+61.0°$ (c=0.53 CH$_2$Cl$_2$); ee=100%
N—[(S)-1-(3-fluoro-4-methoxymethylphenyl)butyl]thiourea Compound IV'.24
$^1$H NMR: 7.39-7.46 (m, Ar, 1H); 6.93-7.07 (m, Ar, 2H and NH, 1H); 5.85 (m, NH$_2$, 2H); 4.45 (s, O—CH$_2$, 2H); 4.35 (m, CH, 1H); 3.38 (s, OCH$_3$, 3H); 1.59-1.88 (m, CH—CH$_2$—CH$_2$, 2H); 1.18-1.40 (m, CH$_2$—CH$_2$—CH$_3$, 2H); 0.85-0.92 (m, CH$_2$—CH$_3$, 3H).
$[\alpha]_D^{19}=+30.5°$ (c=0.77 CH$_2$Cl$_2$); ee=100%.
N—[(S)-2-cyclopropyl-1-(4-methylphenyl)ethyl]thiourea Compound IV'.25
$^1$H NMR: 7.10-7.20 (m, Ar, 4H); 6.93 (m, NH, 1H); 5.75 (m, NH$_2$, 2H); 4.43 (m, CH, 1H); 2.30 (s, CH$_3$, 3H); 1.62-1.73 (m, CH$_2$, 2H); 0.40-0.59 (m, CH and CH$_2$, cyclopropyl, 3H); 0.04-0.13 (m, CH$_2$ cyclopropyl, 2H).
$[\alpha]_D^{19}=+75.5°$ (c=0.42 CH$_2$Cl$_2$); ee=100%.
N—[(S)-1-(3,4-methylenedioxyphenyl)butyl]thiourea Compound IV'.26
F=140° C. $[\alpha]_D^{20}=+40.3$ (c=1.18 CH$_2$Cl$_2$); ee=100%.

b) Production, by chromatography, of optically active thioureas (ee>99%) from racemic thioureas.
N—[(S)-1-phenylpentyl]thiourea Compound IV'.27
Starting with racemic N-(1-phenylpentyl)thiourea, and after separation by chromatography on a Chiracel OJ phase eluting with 95/5 isohexane/ethanol, the S enantiomer is obtained in an enantiomeric purity of 99.8%.
m.p.=147° $[\alpha]_D^{19}=+46.0°$ (c=1.00 CH$_2$Cl$_2$).

PREPARATION OF THE NH AMINOTHIAZOLES IN THE FORM OF AN ENANTIOMERS

Compound II'

[4-(2-Chloro-4-methoxy-5-methylphenyl)-5-methylthiazol-2-yl]-[(1R)-1-(4-fluorophenyl)-2-methoxyethyl]amine Compound II'.1

4.23 g (14.5 mmol) of 2-bromo-1-(2'-chloro-4'-methoxy-5'-methylphenyl)propan-1-one (Compound III.1) and 4.2 ml (30 mmol) of triethylamine are added to 3.28 g (14.3 mmol) of thiourea (Compound IV'1) dissolved in 70 ml of ethanol. The reaction mixture is stirred at 90° C. for 3 hours and is then concentrated under reduced pressure. The residue is taken up in 200 ml of dichloromethane and 100 ml of water. The organic phase is washed with saturated sodium chloride solution, dried over anhydrous sodium sulphate and evaporated to dryness. The crude extract is purified by chromatography on a column of silica gel, eluting with 4/1 (v/v) cyclohexane/ethyl acetate. 5.27 g (12.5 mol) of Compound II'.1 are obtained; yield=87%; MS (MH$^+$) 421.
$^1$H NMR: 7.34-7.44 (m, Ar, 2H); 7.0-7.09 (m, Ar, 3H); 6.83 (s, Ar, 1H); 5.87 (d, NH, 1H); 4.57 (m, CH, 1H); 3.81 (s, OCH$_3$, 3H); 3.46-3.62 (m, OCH$_2$, 2H); 3.35 (s, OCH$_3$, 3H); 2.14 (s, CH$_3$, 3H); 2.04 (s, CH$_3$, 3H).

The following intermediate compounds were obtained in the same way:

TABLE 4

| COMPOUND | R$_1$/R$_2$/R$_3$ | [*] | R$_6$ | R$_7$ | Mass; NMR; m.p. ° C.; $\alpha_D$ |
|---|---|---|---|---|---|
| II'.2 | 2-Cl<br>4-OCH$_3$<br>5-CH$_3$ | R | —CH$_2$OCH$_3$ | 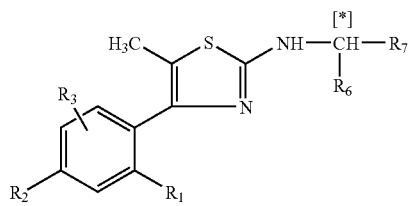 | MS(MH$^+$) 403; $^1$H RMN(DMSO-D$_6$): 7.89(d, NH, 1H); 7.26-7.39(m, Ar, 5H); 7.04(s, Ar, 1H); 6.98(s, Ar, 1H); 4.8(m, CH, 1H); 3.79(s, OCH$_3$, 3H); 3.45-3.62(m, OCH$_2$, 2H); 3.24(s, OCH$_3$, 3H); 2.08(s, CH$_2$, 3H); 1.98(s, CH$_3$, 3H). |

TABLE 4-continued

| COMPOUND | $R_1/R_2/R_3$ | [*] | $R_6$ | $R_7$ | Mass; NMR; m.p. ° C.; $\alpha_D$ |
|---|---|---|---|---|---|
| II'.3 | 2-Cl<br>4-Cl<br>5-CH$_3$ | R | —CH$_2$OCH$_3$ | phenyl (4-methyl) | MS(MH$^+$) 407; $^1$H RMN: 7.25-7.45(m, Ar, 6H); 7.20(s, Ar, 1H); 5.88(d, NH, 1H); 4.57(m, CH, 1H); 3.5-3.67(m, OCH$_2$, 2H); 3.36(s, OCH$_3$, 3H); 2.31(s, CH$_3$, 3H); 2.04(s, CH$_3$, 3H). |
| II'.4 | 2-Cl<br>4-OCH$_3$<br>5-CH$_3$ | R | —CH$_2$OCH$_3$ | 4-Cl-phenyl (4-methyl) | MS(MH$^+$) 437; $^1$H RMN: 7.30-7.38(m, Ar, 4H); 7.08(s, Ar, 1H); 6.83(s, Ar, 1H); 5.86(d, NH, 1H); 4.57(m, CH, 1H); 3.81(s, OCH$_3$, 3H); 3.46-3.70(m, OCH$_2$, 2H); 3.34(s, OCH$_3$, 3H); 2.14(s, CH$_3$, 3H); 2.06(s, CH$_3$, 3H). |
| II'.5 | 2-Cl<br>4-OCH$_3$<br>H | R | —CH$_2$OCH$_3$ | benzodioxole (4-methyl) | MS(MH$^+$) 433; $^1$H RMN: 7.22-7.26(d, Ar, 1H, J=8.5H$_z$), 6.76-6.95(m, Ar, 5H); 5.95(s, O—CH$_2$—O, 2H); 5.83(d, NH, 1H); 4.45(m, CH, 1H); 3.79(s, OCH$_3$, 3H); 3.45-3.60(m, OCH$_2$, 2H); 3.35(s, OCH$_3$, 3H); 2.05(s, CH$_3$, 3H).<br>$[\alpha]^{19}_D = -7.5°$ c = 1.12 CH$_2$Cl$_2$ |
| II'.6 | 2-Cl<br>4-OCH$_3$<br>5-CH$_3$ | R | —CH$_2$OCH$_3$ | benzodioxole (4-methyl) | MS(MH$^+$) = 447; 70<br>$[\alpha]^{19}_D = -6.0°$ (c = 0.8 CH$_2$Cl$_2$) |
| II'.7 | 2-Cl<br>4-OCH$_3$<br>5-CH$_3$ | R | —CH$_2$OCH$_3$ | 4-ethylphenyl (4-methyl) | MS(MH$^+$) = 431; $^1$H RMN: 7.16-7.35(m, Ar, 4H); 7.10(s, Ar, 1H); 6.83(s, Ar, 1H); 5.86(d, NH, 1H); 4.54(m, CH, 1H); 3.81(s, OCH$_3$, 3H); 3.48-3.64(m, OCH$_2$, 2H); 3.34(s, OCH$_3$, 3H); 2.65(q, J=7.6H$_z$, CH$_2$CH$_3$, 2H); 2.14(s, CH$_3$, 3H); 2.05(s, CH$_3$, 3H); 1.23(t, J=7.6H$_z$ CH$_2$CH$_3$, 3H). |
| II'.8 | 2-Cl<br>4-OCH$_3$<br>5-CH$_3$ | R | —CH$_2$OCH$_3$ | 2-F-3-Cl-phenyl (4-methyl) | MS(MH$^+$) = 455; $^1$H RMN: 7.12-7.40(m, Ar, 3H); 7.08(s, Ar, 1H); 6.83(s, Ar, 1H); 5.85-5.87(m, NH, 1H); 4.57-4.65(m, CH, 1H); 3.81(s, OCH$_3$, 3H); 3.48-3.70(m, OCH$_2$, 2H); 3.35(s, OCH$_3$, 3H); 2.15(s, CH$_3$, 3H); 2.08(s, CH$_3$, 3H). |
| II'.9 | 2-Cl<br>4-OCH$_3$<br>5-CH$_3$ | R | —CH$_2$OCH$_3$ | 2-F-3-CH$_3$-phenyl (4-methyl) | MS(MH$^+$) = 435; $^1$H RMN: 7.06-7.20(m, Ar, 4H); 6.83(s, Ar, 1H); 5.83-5.85(m, NH, 1H); 4.51-4.58(m, CH, 1H); 3.81(s, OCH$_3$, 3H); 3.48-3.65(m, OCH$_2$, 2H); 3.35(s, OCH$_3$, 3H); 2.25(s, CH$_3$, 3H); 2.15(s, CH$_3$, 3H); 2.07(s, CH$_3$, 3H). |
| II'.10 | 2-Cl<br>4-OCH$_3$<br>H | S | —(CH$_2$)$_2$CH$_3$ | phenyl | MS(MH$^+$) = 386; $^1$H RMN: 7.24-7.34(m, Ar, 5H); 7.24(d, J=8.5H$_z$, Ar, 1H); 6.94(d, J=2.5H$_z$, Ar, 1H); 6.79(dd, J$_1$=8.5H$_z$ J$_2$=2.5H$_z$, Ar, 1H); 5.50(d, NH, 1H); 4.29(m, CH, 1H); 3.79(s, OCH$_3$, 3H); 2.04(s, CH$_3$, 3H); 1.68-1.88(m, CH$_2$, 2H); 1.25-1.45(m, CH$_2$, 2H); 0.90(t, CH$_3$, 3H). |

TABLE 4-continued

| COMPOUND | $R_1/R_2/R_3$ | [*] | $R_6$ | $R_7$ | Mass; NMR; m.p. °C.; $\alpha_D$ |
|---|---|---|---|---|---|
| II'.11 | 2-Cl<br>4-OCH$_3$<br>5-CH$_3$ | S | —(CH$_2$)$_2$CH$_3$ | phenyl | MS(MH$^+$) 401; 64<br>[α]$^{19}_D$ = −12.0° (c = 0.86 CH$_2$Cl$_2$) |
| II'.12 | 2-Cl<br>4-OCH$_3$<br>5-CH$_3$ | S | —CH$_2$-cyclopropyl | phenyl | MS(MH$^+$) = 413; $^1$H RMN: 7.21-7.38(m, Ar, 5H); 7.11(s, Ar, 1H); 6.82(s, Ar, 1H); 5.77(d, NH, 1H); 4.38(m, CH, 1H); 3.80(s, OCH$_3$, 3H); 2.14(s, CH$_3$, 3H); 2.05(s, CH$_3$, 3H); 1.65-1.75(m, CH$_2$, 2H); 0.58-0.70(m, CH cyclopropyl, 1H); 0-0.5(m, 2CH$_2$ cyclopropyl, 4H). |
| II'.13 | 2-Cl<br>4-OCH$_3$<br>H | S | —CH$_2$-cyclopropyl | phenyl | MS(MH$^+$) = 399; $^1$H RMN: 7.26-7.40(m, Ar, 5H); 7.25(d, J=8.5H$_z$, Ar, 1H); 6.96(d, J=2.6H$_z$, Ar, 1H); 6.80(dd, J$_1$=8.5H$_z$, J$_2$=2.6H$_z$, Ar, 1H); 4.70(m, NH, 1H); 4.42(m, CH, 1H); 3.80(s, OCH$_3$, 3H); 2.06(s, CH$_3$, 3H); 1.72(m, CH$_2$, 2H); 0.62-0.66(m, CH cyclopropyl, 1H); 0.04-0.49(m, 2CH$_2$ cyclopropyl, 4H). |
| II'.14 | 2-Cl<br>4-OCH$_3$<br>5-CH$_3$ | S | —CH$_2$-cyclopropyl | 4-F-phenyl | MS(MH$^+$) 431<br>F = 71°; [α]$^{22}_D$ = +17.7° (c = 0.585 CH$_2$Cl$_2$) |
| II'.15 | 2-Cl<br>4-OCH$_3$<br>5-CH$_3$ | S | —(CH$_2$)$_3$CH$_3$ | phenyl | MS(MH$^+$) 415; $^1$H RMN: 7.25-7.35(m, Ar, 5H); 7.10(s, Ar, 1H); 6.83(s, Ar, 1H); 5.46(d, NH, 1H); 4.26(m, CH, 1H); 3.81(s, OCH$_3$, 3H); 2.14(s, CH$_3$, 3H); 2.05(s, CH$_3$, 3H); 1.76-1.82(m, CHCH$_2$CH$_2$, 2H); 1.2-1.41(m, CH$_2$CH$_2$CH$_3$, 4H); 0.85(d, CH$_3$, 3H). [α]$^{23}_D$ = 9.5° (c = 1.0 CH$_2$Cl$_2$) |
| II'.16 | 2-Cl<br>4-OCH$_3$<br>H | S | —(CH$_2$)$_3$CH$_3$ | phenyl | $^1$H RMN: 7.27-7.35(m, Ar, 5H); 7.23(d, J=8.5Hz, Ar, 1H); 6.94(d, J=2.5H$_z$, Ar, 1H); 6.79(dd, J$_1$=8.5H$_z$, J$_2$=2.5H$_z$, Ar, 1H); 5.44(d, NH, 1H); 4.28(m, CH, 1H); 3.79(s, OCH$_3$, 3H); 2.05(s, CH$_3$, 3H); 1.7-1.83(m, CH—CH$_2$—CH$_2$, 2H); 1.2-1.33(m, —CH$_2$CH$_2$CH$_3$, 4H); 0.85(t, CH$_2$CH$_3$, 3H). |
| II'.17 | 2-Cl<br>4-OCH$_3$<br>H | R | —CH$_2$OCH$_3$ | 4-CH$_2$OCH$_3$-phenyl | MS(MH$^+$) = 433; $^1$H RMN; 7.40(d, Ar, 2H); 7.32(d, Ar, 2H); 7.23(d, Ar, 1H); 6.94(d, Ar, 1H); 5.85(d, NH, 1H); 4.58(m, CH, 1H); 4.40(s, OCH$_2$, 2H); 3.80(s, OCH$_3$, 3H); 3.52-3.65(m, OCH$_2$, 2H); 3.39(s, OCH$_3$, 3H); 3.35(s, OCH$_3$, 3H); 2.04(s, CH$_3$, 3H). |
| II'.18 | 2-Cl<br>4-OCH$_3$<br>5-CH$_3$ | R | —CH$_2$OCH$_3$ | 4-CH$_2$OCH$_3$-phenyl | MS(MH$^+$) = 447; $^1$H RMN: 7.41(d, Ar, 2H); 7.32(d, Ar, 2H); 7.10(s, Ar, 1H); 6.83(s, Ar, 1H); 5.89(m, NH, 1H); 4.57(m, CH, 1H); 4.44(s, OCH$_2$, 2H); 3.81(s, OCH$_3$, 3H); 3.57-3.65(m, OCH$_2$, 2H); 3.39(s, OCH$_3$, 3H); 3.35(s, OCH$_3$, 3H); 2.15(s, CH$_3$, 3H); 2.05(s, CH$_3$, 3H). |

TABLE 4-continued

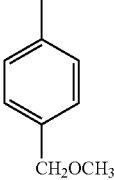

| COMPOUND | R₁/R₂/R₃ | [*] | R₆ | R₇ | Mass; NMR; m.p. ° C.; α_D |
|---|---|---|---|---|---|
| II'.19 | 2-Cl<br>4-OCH₃<br>5-CH₃ | S | —(CH₂)₂CH₃ | 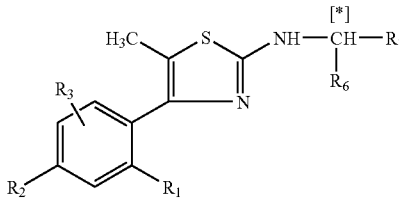 | MS(MH⁺) = 445; ¹H RMN: 7.26-7.36(m, Ar, 4H); 7.10(s, Ar, 1H); 6.83(s, Ar, 1H); 5.47-5.44(m, NH, 1H); 4.43(s, O—CH₂, 2H); 4.33-4.23(m, CH, 1H); 3.81(s, OCH₃, 3H); 3.39(s, OCH₃, 3H); 2.14(s, CH₃, 3H); 2.05(s, CH₃, 3H); 1.91-1.62(m, CH₂, 2H); 1.48-1.21(m, CH₃, 3H). |
| II'.20 | 2-Cl<br>4-OCH₃<br>5-CH₃ | S | —(CH₂)₃CH₃ | 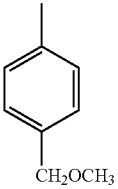 | MS(MH⁺) = 459; ¹H RMN: 7.27-7.35(m, Ar, 4H); 7.10(s, Ar, 1H); 6.83(s, Ar, 1H); 5.43(m, NH, 1H); 4.43(s, OCH₂, 2H); 4.22-4.31(m, CH, 1H); 3.81(s, CH₃, 3H); 3.39(s, OCH₃, 3H); 2.15(s, CH₃, 3H); 2.05(s, CH₃, 3H); 1.73-1.82(m, CH₂, 2H); 1.21-1.36(m, —CH₂—CH₂, 4H); 0.82-0.88(m, CH₃, 3H). |
| II'.21 | 2-Cl<br>4-OCH₃<br>5-CH₃ | S | —(CH₂)₃CH₃ | 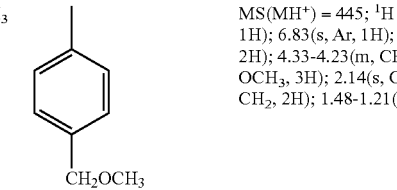 | MS(MH⁺) = 433; ¹H RMN: 7.25-7.32(m, Ar, 2H); 7.10(s, Ar, 1H); 6.95-7.06(m, Ar, 2H); 6.82(s, Ar, 1H); 5.52(d, J=5.7Hz, NH, 1H); 4.20-4.30(m, CH, 1H); 3.81(s, OCH₃, 3H); 2.14(s, CH₃, 3H); 2.06(s, CH₃, 3H); 1.69-1.82(m, CH₂, 2H); 1.21-1.37(m, CH₂CH₂, 4H); 0.85(t, CH₃, 3H). |
| II'.22 | 2-Cl<br>4-OCH₃<br>H | S | 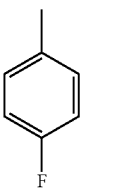 | 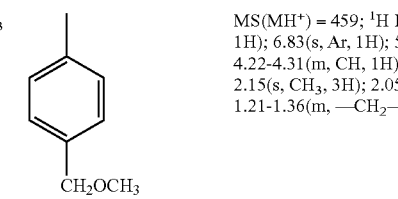 | MS(MH⁺) = 385; ¹H RMN: 7.28-7.43(m, Ar, 5H); 7.23(d, J=8.5Hz, Ar, 1H); 6.87(d, J=2.5Hz, Ar, 1H); 6.80(dd, J₁=8.5Hz, J₂=2.5Hz, Ar, 1H); 5.32(m, NH, 1H); 3.79(s, OCH₃, 3H); 3.74(m, CH, 1H); 2.03(s, CH₃, 3H); 1.15-1.30(m, CH cyclopropyl, 1H); 0.38-0.67(m, 2CH₂ cyclopropyl, 4H). |
| II'.23 | 2-Cl<br>4-OCH₃<br>5-CH₃ | S |  | 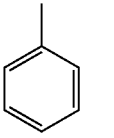 | MS(MH⁺) = 399; ¹H RMN: 7.26-7.43(m, Ar, 5H); 7.10(s, Ar, 1H); 6.83(s, Ar, 1H); 5.63(m, NH, 1H); 3.81(s, OCH₃, 3H); 3.74(m, CH, 1H); 2.36(s, CH₃, 3H); 2.04(s, CH₃, 3H); 1.15-1.30(m, CH cyclopropyl, 1H); 0.35-0.67(m, 2CH₂ cyclopropyl, 4H). |
| II'.24 | 2-Cl<br>4-OCH₃<br>5-CH₃ | S | —(CH₂)₂CH₃ | 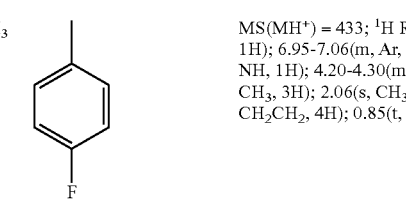 | MS(MH⁺) = 433; ¹H RMN(DMSO-D₆): 7.82(d, J=8.2Hz, NH, 1H); 7.10-7.22(m, Ar, 3H); 7.03(s, Ar, 1H); 6.98(s, Ar, 1H); 4.41-4.52(m, CH, 1H); 3.79(s, OCH₃, 3H); 2.17(d, J=1.65Hz, CH₃, 3H); 2.08(s, CH₃, 3H); 1.97(s, CH₃, 3H); 1.57-1.75(m, CH₂, 2H); 1.23-1.37(m, CH₂, 2H); 0.84(t, CH₃, 3H). |
| II'.25 | 2-Cl<br>4-OCH₃<br>5-CH₃ | S | —(CH₂)₃CH₃ |  | MS(MH⁺) = 447; ¹H RMN: 7.10-7.17(m, Ar, 2H); 6.95-7.02(m, Ar, 2H); 6.83(s, Ar, 1H); 5.43(m, NH, 1H); 4.19-4.26(m, CH, 1H); 3.81(s, OCH₃, 3H); 2.25(d, J=1.84Hz, CH₃, 3H); 2.14(s, CH₃, 3H); 2.06(s, CH₃, 3H); 1.70-1.85(m, CH₂, 2H); 1.19-1.35(m, CH₂CH₂, 4H); 0.84(t, CH₃, 3H). |

TABLE 4-continued

Structure: 5-methyl-thiazole core with H3C at 5-position, NH-CH(R6)-R7 at 2-position ([*] on CH), and phenyl group at 4-position bearing R1 (2-), R2 (4-), R3 (5-) substituents.

| COMPOUND | R1/R2/R3 | [*] | R6 | R7 | Mass; NMR; m.p. °C.; α_D |
|---|---|---|---|---|---|
| II'.26 | 2-Cl 4-OCH3 5-CH3 | S | CH2-cyclopropyl | 3-fluoro-4-methylphenyl | MS(MH+) = 445; ¹H RMN: 7.00-7.17(m, Ar, 4H); 6.83(s, Ar, 1H); 5.66(m, NH, 1H); 4.30-4.40(m, CH, 1H); 3.81(s, OCH3, 3H); 2.25(d, J=1.84Hz, CH3, 3H); 2.14(s, CH3, 3H); 2.06(s, CH3, 3H); 1.64-1.71(m, CH2, 2H); 0.54-0.63(m, CH cyclopropyl, 1H); 0.40-0.52(m, CH2 cyclopropyl, 2H) 0.06-0.15(m, CH2 cyclopropyl, 2H). |
| II'.27 | 2-Cl 4-OCH3 5-CH3 | S | —(CH2)2CH3 | 4-fluorophenyl | MS(MH+) = 419; ¹H RMN: 7.25-7.33(m, Ar, 2H); 6.95-7.09(m, Ar, 3H); 6.83(s, Ar, 1H); 5.49(m, NH, 1H); 4.22-4.32(m, CH, 1H); 3.81(s, OCH3, 3H); 2.14(s, CH3, 3H); 2.06(s, CH3, 3H); 1.70-1.85(m, CH2, 2H); 1.18-1.37(m, CH2, 2H); 0.90(t, CH3, 3H). |
| II'.28 | 2-Cl 4-OCH3 5-CH3 | S | —(CH2)2CH3 | 2-fluoro-4-(CH2OCH3)phenyl | MS(MH+) = 463; ¹H RMN: 7.32-7.40(m, Ar, 1H); 7.01-7.14(m, Ar, 3H); 6.83(s, Ar, 1H); 5.41(d, J=5.9Hz, NH, 1H); 4.48(s, OCH2, 2H); 4.24-4.34(m, CH, 1H); 3.81(s, OCH3, 3H); 3.41(s, OCH3, 3H); 2.14(s, CH3, 3H); 2.06(s, CH3, 3H); 1.65-1.83(m, CH2, 2H); 1.20-1.42(m, CH2, 2H); 0.90(t, CH3, 3H). |
| II'.29 | 2-Cl 4-OCH3 5-CH3 | S | CH2-cyclopropyl | 4-chlorophenyl | MS(MH+) = 447; ¹H RMN: 7.30(s, Ar, 4H); 7.08(s, Ar, 1H); 6.83(s, Ar, 1H); 5.69(m, NH, 1H); 4.35-4.45(m, CH, 1H); 3.81(s, OCH3, 3H); 2.14(s, CH3, 3H); 2.06(s, CH3, 3H); 1.64-1.72(m, CH2, 2H); 0.53-0.63(m, CH cyclopropyl, 1H); 0.42-0.52(m, CH2 cyclopropyl, 2H); 0.02-0.15(m, CH2 cyclopropyl, 2H). |
| II'.30 | 2-Cl 4-OCH3 5-CH3 | S | CH2-cyclopropyl | 4-methylphenyl | MS(MH+) = 427; ¹H RMN: 7.25(d, J=8.1Hz, Ar, 2H); 7.13(d, J=8.1Hz, Ar, 2H); 7.10(s, Ar, 1H); 6.83(s, Ar, 1H); 5.76(m, NH, 1H); 4.29-4.39(m, CH, 1H); 3.81(s, OCH3, 3H); 2.33(s, CH3, 3H); 2.14(s, CH3, 3H); 2.05(s, CH3, 3H); 1.65-1.72(m, CH2, 2H); 0.54-0.69(m, CH cyclopropyl, 1H); 0.35-0.50(m, CH2 cyclopropyl, 2H); 0.06-0.15(m, CH2 cyclopropyl, 2H). |
| II'.31 | 2-Cl 4-OCH3 5-CH3 | S | CH2-cyclobutyl | 4-fluorophenyl | MS(MH+) = 445; ¹H RMN: 7.23-7.30(m, Ar, 2H); 6.95-7.09(m, Ar, 3H); 6.81(s, Ar, 1H); 5.57(m, NH, 1H); 4.11-4.21(m, CH, 1H); 3.81(s, OCH2, 3H); 2.14(s, CH3, 3H); 2.06(s, CH3, 3H); 1.50-2.25(m, CH2, CH and (CH2)3 cyclobutyl, 9H). |
| II'.32 | 2-Cl 4-OCH3 5-CH3 | S | CH2-cyclopropyl | 4-bromophenyl | MS(MH+) = 491; ¹H RMN: 7.41-7.48(m, Ar, 2H); 7.20-7.25(m, Ar, 2H); 7.10(s, Ar, 1H); 6.81(s, Ar, 1H); 5.96(m, NH, 1H); 4.29-4.39(m, CH, 1H); 3.81(s, OCH3, 3H); 2.15(s, CH3, 3H); 2.05(s, CH3, 3H); 1.56-1.67(m, CH2, 2H); 0.51-0.65(m, CH cyclopropyl, 1H); 0.34-0.50(m, CH2 cyclopropyl, 2H); 0.03-0.14(m, CH2 cyclopropyl, 2H). |

TABLE 4-continued

| COMPOUND | $R_1/R_2/R_3$ | [*] | $R_6$ | $R_7$ | Mass; NMR; m.p. °C.; $\alpha_D$ |
|---|---|---|---|---|---|
| II'.33 | 2-Cl<br>4-OCH$_3$<br>5-CH$_3$ | S | 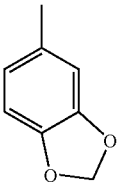 |  | MS(MH$^+$) = 457; $^1$H RMN: 7.10(s, Ar, 1H); 6.74-6.86(m, Ar, 4H); 5.94(s, OCH$_2$O, 2H); 5.93(s, NH, 1H); 4.24-4.34(m, CH, 1H); 3.81(s, OCH$_3$, 3H); 2.15(s, CH$_3$, 3H); 2.07(s, CH$_3$, 3H); 1.64-1.72(m, CH$_2$, 2H); 0.51-0.63(m, CH cyclopropyl, 1H); 0.40-0.50(m, CH$_2$ cyclopropyl, 2H); 0.02-0.13(m, CH$_2$ cyclopropyl, 2H). |
| II'.34 | 2-Cl<br>4-OCH$_3$<br>H | S | 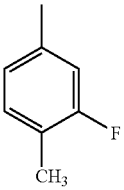 |  | MS(MH$^+$) = 431; $^1$H RMN: 6.97-7.28(m, Ar, 5H); 6.79-6.85(m, Ar, 1H); 6.16(m, NH, 1H); 4.32-4.42(m, CH, 1H); 3.81(s, OCH$_3$, 3H); 2.26(d, J=1.85Hz, CH$_3$, 3H); 2.07(s, CH$_3$, 3H); 1.69-1.76(m, CH$_2$, 2H); 0.53-0.66(m, CH cyclopropyl, 1H); 0.40-0.50(m, CH$_2$ cyclopropyl, 2H) 0.04-0.14(m, CH$_2$ cyproyl, 2H). |
| II'.35 | 2-OCH$_3$<br>4-OCH$_3$<br>5-CH$_3$ | S | 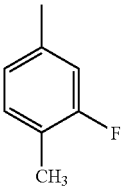 |  | MS(MH$^+$) = 441; $^1$H RMN: 7.00-7.18(m, Ar, 4H); 6.45(s, Ar, 1H); 5.98(m, NH, 1H); 4.28-4.38(m, CH, 1H); 3.85(s, OCH$_3$, 3H); 3.79(s, OCH$_3$, 3H); 2.26(d, J=1.82Hz, CH$_3$, 3H); 2.14(s, CH$_3$, 3H); 2.07(s, CH$_3$, 3H); 1.66-1.72(m, CH$_2$, 2H); 0.53-0.68(m, CH cyclopropyl, 1H); 0.40-0.50(m, CH$_2$ cyclopropyl, 2H); 0.04-0.14(m, CH$_2$ cyclopropyl, 2H). |
| II'.36 | 2-CH$_3$<br>4-OCH$_3$<br>5-CH$_3$ | S | 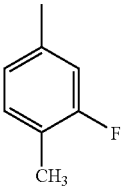 | 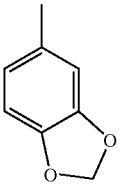 | MS(MH$^+$) = 425; $^1$H RMN: 6.96-7.17(m, Ar, 4H); 6.64(s, Ar, 1H); 5.83(m, NH, 1H); 4.32-4.42(m, CH, 1H); 3.80(s, OCH$_3$, 3H); 2.25(d, J=1.85Hz, CH$_3$, 3H); 2.14(s, 2CH$_3$, 6H); 2.07(s, CH$_3$, 3H); 1.63-1.70(m, CH$_2$, 2H); 0.53-0.66(m, CH cyclopropyl, 1H); 0.39-0.50(m, CH$_2$ cyclopropyl, 2H); 0.02-0.14(m, CH$_2$ cyclopropyl, 2H). |
| II'.37 | 2-Cl<br>4-OCH$_3$<br>5-CH$_3$ | S | —(CH$_2$)$_2$CH$_3$ | | MS(MH$^+$) = 445; $^1$H RMN: 7.10(s, Ar, 1H); 6.72-6.82(m, Ar, 4H); 5.93(s, OCH$_2$O, 2H); 5.60(d, NH, 1H); 4.12-4.22(m, CH, 1H); 3.80(s, OCH$_3$, 3H); 2.14(s, CH$_3$, 3H); 2.06(s, CH$_3$, 3H); 1.64-1.85(m, CH$_2$, 2H); 1.22-1.45(m, CH$_2$, 2H); 0.85-0.89(m, CH$_3$, 3H). |

PREPARATION OF THE N-SUBSTITUTED AMINOTHIAZOLES IN THE FORM OF AN ENANTIOMER

Example 25

[4-(2-Chloro-4-methoxy-5-methylphenyl)-5-methylthiazol-2-yl]-[(1R)-1-(4-fluorophenyl)-2-methoxyethyl]prop-2-ynylamine A solution of 2.5 g (5.9 mmol) of Compound II'.1 in 30 ml of dimethylformamide is stirred at 0° C. and 260 mg (6.5 mmol) of sodium hydride in 60% in oil are added. The reaction mixture is stirred for 20 minutes at 0° C., followed by addition of 0.83 ml (7.5 mmol) of an 80% solution of propargyl bromide in toluene. The reaction mixture is stirred for one hour at 10° C., followed by addition, at 0° C., of 2 ml of ethanol and then 50 ml of ethyl acetate. The mixture is extracted with 200 ml of ethyl acetate. The organic phase is washed with water and then with saturated sodium chloride solution, dried over anhydrous sodium sulphate and then evaporated to dryness. The crude residue is chromatographed on a column of silica gel, eluting with 9/1 (v/v) cyclohexane/ethyl acetate. 2.14 g of a gummy pure product are obtained; yield=80%; MS (MH$^+$) 459

$^1$H NMR: 7.35-7.46 (m, Ar, 2H); 7.14 (s, Ar, 1H); 6.95-7.07 (m, Ar, 2H); 6.81 (s, Ar, 1H); 5.54 (m, CH, 1H); 4.15 (dd, $J_1$=18 Hz, $J_2$=2.4 Hz, CH$_2$—N, 1H); 4.00-4.08 (m, OCH$_2$, 2H); 3.98 (dd, $J_1$=18 Hz, $J_2$=2.4 Hz, CH$_2$—N, 1H); 3.892 (s, OCH$_3$, 3H); 3.40 (s, OCH$_3$, 3H); 2.18 (t, J=2.4 Hz, CH propargyl, 1H); 2.17 (s, CH$_3$, 3H); 2.16 (s, CH$_3$, 3H).

$[\alpha]_D^{19}$ = −127° C. (c=0.99 CH$_2$Cl$_2$)

Supercritical chiral HPLC: ee=99.4%

TABLE 5

| EXAMPLES | R$_1$/R$_2$/R$_3$ | [*] | R$_6$ | R$_7$ | Mass; m.p. °C. (HCl); α$_D$; ee |
|---|---|---|---|---|---|
| 26 | 2-Cl<br>4-OCH$_3$<br>5-CH$_3$ | R | —CH$_2$OCH$_3$ | 4-chlorophenyl | MS(MH$^+$) = 475<br>81; $[\alpha]_D^{19}$ = −153.0° (c = 1.00 CH$_2$Cl$_2$)<br>ee = 98.4% |
| 27 | 2-Cl<br>4-OCH$_3$<br>H | R | —CH$_2$OCH$_3$ | benzo[1,3]dioxol-5-yl | MS(MH$^+$) = 471<br>100; $[\alpha]_D^{19}$ = −132.0° (c = 0.84 CH$_2$Cl$_2$)<br>ee = 100% |
| 28 | 2-Cl<br>4-OCH$_3$<br>5-CH$_3$ | R | —CH$_2$OCH$_3$ | benzo[1,3]dioxol-5-yl | MS(MH$^+$) = 485<br>97; $[\alpha]_D^{19}$ = −161.0° (c = 0.97 CH$_2$Cl$_2$) |
| 29 | 2-Cl<br>4-OCH$_3$<br>5-CH$_3$ | R | —CH$_2$OCH$_3$ | 4-ethylphenyl | MS(MH$^+$) = 469<br>63; $[\alpha]_D^{20}$ = −133.0° (c = 1.05 CH$_2$Cl$_2$) |
| 30 | 2-Cl<br>4-OCH$_3$<br>5-CH$_3$ | R | —CH$_2$OCH$_3$ | 4-chloro-3-fluorophenyl | MS(MH$^+$) = 493<br>75; $[\alpha]_D^{20}$ = −137.5° (c = 1.005 CH$_2$Cl$_2$) |
| 31 | 2-Cl<br>4-OCH$_3$<br>5-CH$_3$ | R | —CH$_2$OCH$_3$ | 3-fluoro-4-methylphenyl | MS(MH$^+$) = 473<br>86; $[\alpha]_D^{20}$ = −130.1° (c = 1.095 CH$_2$Cl$_2$) |
| 32 | 2-Cl<br>4-OCH$_3$<br>H | S | —(CH$_2$)$_2$CH$_3$ | phenyl | MS(MH$^+$) = 425<br>84; $[\alpha]_D^{20}$ = −206.0° (c = 1.00 CH$_2$Cl$_2$)<br>ee = 98.9% |

TABLE 5-continued

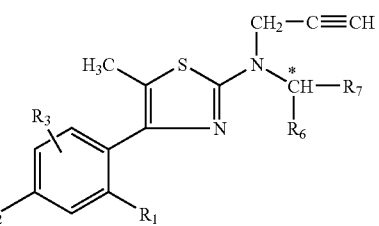

| EXAMPLES | R₁/R₂/R₃ | [*] | R₆ | R₇ | Mass; m.p. ° C. (HCl); α_D; ee |
|---|---|---|---|---|---|
| 33 | 2-Cl<br>4-OCH₃<br>5-CH₃ | S | —(CH₂)₂CH₃ | 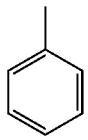 | MS(MH⁺) = 439<br>95; [α]$^{20}_D$ = −175° (c = 0.65 methanol)<br>ee = 99.4% |
| 34 | 2-Cl<br>4-OCH₃<br>5-CH₃ | S | 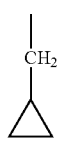 | 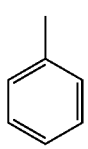 | MS(MH⁺) = 451<br>102; [α]$^{20}_D$ = −231.0° (c = 1.14 CH₂Cl₂)<br>ee = 100% |
| 35 | 2-Cl<br>4-OCH₃<br>H | S |  | 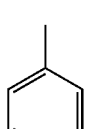 | MS(MH⁺) = 437<br>74; [α]$^{19}_D$ = −208.0° (c = 1.02 CH₂Cl₂)<br>ee = 100% |
| 36 | 2-Cl<br>4-OCH₃<br>5-CH₃ | S |  | 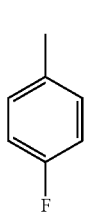 | MS(MH+) = 469<br>94; [α]$^{22}_D$ = −214.0° (c = 0.685 CH₂Cl₂) |
| 37 | 2-Cl<br>4-OCH₃<br>5-CH₃ | S | —(CH₂)₃CH₃ | 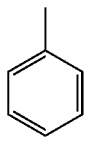 | MS(MH⁺) = 453<br>75; [α]$^{20}_D$ = −207.0° (c = 0.97 CH₂Cl₂)<br>ee = 99.5% |
| 38 | 2-Cl<br>4-OCH₃<br>H | S | —(CH₂)₃CH₃ | 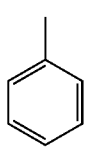 | MS(MH⁺) = 439<br>88; [α]$^{20}_D$ = −174.0° (c = 1.00 CH₂Cl₂)<br>ee = 99.5% |
| 39 | 2-Cl<br>4-OCH₃<br>H | R | —CH₂OCH₃ | 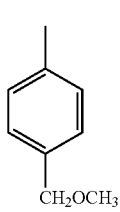 | MS(MH⁺) = 471<br>47; [α]$^{19}_D$ = −140.4° (c = 0.72 CH₂Cl₂)<br>ee = 97.3% |

TABLE 5-continued

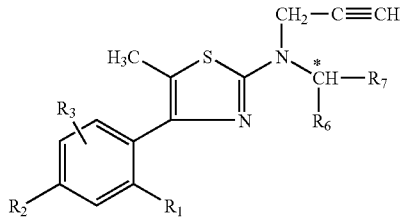

| EXAMPLES | R₁/R₂/R₃ | [*] | R₆ | R₇ | Mass; m.p. ° C. (HCl); α_D; ee |
|---|---|---|---|---|---|
| 40 | 2-Cl<br>4-OCH₃<br>5-CH₃ | R | —CH₂OCH₃ | 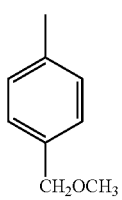 | MS(MH⁺) = 485<br>54; $[\alpha]^{20}_D = -132.2°$ (c = 0.93 CH₂Cl₂)<br>ee = 97.3% |
| 41 | 2-Cl<br>4-OCH₃<br>5-CH₃ | S | —(CH₂)₂CH₃ | 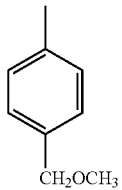 | MS(MH⁺) = 483<br>56; $[\alpha]^{20}_D = -178.0°$ (c = 0.38 CH₂Cl₂) |
| 42 | 2-Cl<br>4-OCH₃<br>5-CH₃ | S | —(CH₂)₃CH₃ | 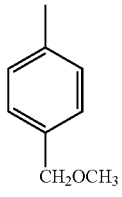 | MS(MH⁺) = 497<br>52; $[\alpha]^{20}_D = -165.2°$ (c = 0.97 CH₂Cl₂) |
| 43 | 2-Cl<br>4-OCH₃<br>5-CH₃ | R | —CH₂OCH₃ | 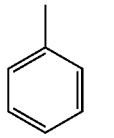 | MS(MH⁺) = 441<br>76; $[\alpha]^{19}_D = -120.0°$ (c = 0.92 CH₂Cl₂)<br>ee = 99.7% |
| 44 | 2-Cl<br>4-Cl<br>5-CH₃ | R | —CH₂OCH₃ | 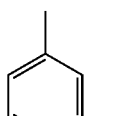 | MS(MH⁺) = 445<br>69; $[\alpha]^{19}_D = -103.0°$ (c = 0.73 CH₂Cl₂)<br>ee = 99.7% |
| 45 | 2-Cl<br>4-OCH₃<br>5-CH₃ | S | —(CH₂)₃CH₃ | 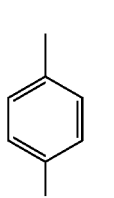 | MS(MH⁺) = 471<br>77; $[\alpha]^{19}_D = -213°$ (c = 1.06 CH₂Cl₂) |
| 46 | 2-Cl<br>4-OCH₃<br>H | S |  | 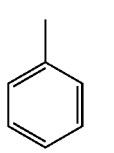 | MS(MH⁺) = 423<br>73; $[\alpha]^{19}_D = -10.5°$ (c = 0.93 CH₂Cl₂) |

TABLE 5-continued

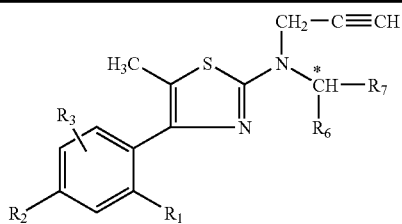

| EXAMPLES | R₁/R₂/R₃ | [*] | R₆ | R₇ | Mass; m.p. ° C. (HCl); α_D; ee |
|---|---|---|---|---|---|
| 47 | 2-Cl<br>4-OCH₃<br>5-CH₃ | S | cyclopropyl | phenyl | MS(MH⁺) = 437<br>106; $[\alpha]^{19}_D = -106°$ (c = 1.0 CH₂Cl₂) |
| 48 | 2-Cl<br>4-OCH₃<br>5-CH₃ | S | —(CH₂)₂CH₃ | 3-F, 4-CH₃-phenyl | MS(MH⁺) = 471<br>81; $[\alpha]^{19}_D = -225°$ (c = 0.85 CH₂Cl₂)<br>ee = 99% |
| 49 | 2-Cl<br>4-OCH₃<br>5-CH₃ | S | —(CH₂)₃CH₃ | 3-F, 4-CH₃-phenyl | MS(MH⁺) = 485<br>73; $[\alpha]^{20}_D = -197°$ (c = 0.45 CH₂Cl₂)<br>ee = 98.5% |
| 50 | 2-Cl<br>4-OCH₃<br>5-CH₃ | S | —CH₂-cyclopropyl | 3-F, 4-CH₃-phenyl | MS(MH⁺) = 483<br>115; $[\alpha]^{20}_D = -230°$ (c = 0.77 CH₂Cl₂)<br>ee = 99.2% |
| 51 | 2-Cl<br>4-OCH₃<br>5-CH₃ | S | —(CH₂)₂CH₃ | 4-F-phenyl | MS(MH⁺) = 457<br>84; $[\alpha]^{20}_D = -188°$ (c = 0.98 CH₂Cl₂)<br>ee = 98.4% |
| 52 | 2-Cl<br>4-OCH₃<br>5-CH₃ | S | —(CH₂)₂CH₃ | 3-F, 4-CH₂OCH₃-phenyl | MS(MH⁺) = 501<br>79; $[\alpha]^{20}_D = -160°$ (c = 0.43 CH₂Cl₂) |
| 53 | 2-Cl<br>4-OCH₃<br>5-CH₃ | S | —CH₂-cyclopropyl | 4-Cl-phenyl | MS(MH⁺) = 447<br>98; $[\alpha]^{20}_D = -187°$ (c = 0.90 CH₂Cl₂)<br>ee = 100% |

TABLE 5-continued

| EXAMPLES | R₁/R₂/R₃ | [*] | R₆ | R₇ | Mass; m.p. °C. (HCl); α_D; ee |
|---|---|---|---|---|---|
| 54 | 2-Cl<br>4-OCH₃<br>5-CH₃ | S | CH₂-cyclopropyl | 4-CH₃-phenyl | MS(MH⁺) = 465<br>105; [α]²⁰_D = −218° (c = 0.92 CH₂Cl₂) |
| 55 | 2-Cl<br>4-OCH₃<br>5-CH₃ | S | CH₂-cyclobutyl | 4-F-phenyl | MS(MH⁺) = 483<br>89; [α]²⁰_D = −182° (c = 1.05 methanol)<br>ee = 99% |
| 56 | 2-Cl<br>4-OCH₃<br>5-CH₃ | S | CH₂-cyclopropyl | 4-Br-phenyl | MS(MH⁺) = 530<br>141; [α]²⁰_D = −298° (c = 0.41 CH₂Cl₂) |
| 57 | 2-Cl<br>4-OCH₃<br>5-CH₃ | S | CH₂-cyclopropyl | benzo[1,3]dioxol-5-yl | MS(MH⁺) = 495<br>131; [α]¹⁹_D = −219° (c = 0.80 CH₂Cl₂) |
| 58 | 2-Cl<br>4-OCH₃<br>H | S | CH₂-cyclopropyl | 3-F-4-CH₃-phenyl | MS(MH⁺) = 469<br>75; [α]²⁰_D = −216° (c = 0.825 CH₂Cl₂) |
| 59 | 2-OCH₃<br>4-OCH₃<br>5-CH₃ | S | CH₂-cyclopropyl | 3-F-4-CH₃-phenyl | MS(MH⁺) = 479<br>96; [α]²⁰_D = −208° (c = 0.79 CH₂Cl₂) |

TABLE 5-continued

| EXAMPLES | R₁/R₂/R₃ | [*] | R₆ | R₇ | Mass; m.p. ° C. (HCl); α$_D$; ee |
|---|---|---|---|---|---|
| 60 | 2-CH₃<br>4-OCH₃<br>5-CH₃ | S | 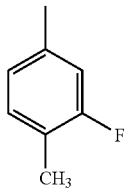 | 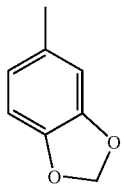 | MS(MH⁺) = 463<br>114; [α]$^{20}_D$ = −205° (c = 0.82 CH₂Cl₂) |
| 61 | 2-Cl<br>4-OCH₃<br>5-CH₃ | S | —(CH₂)₂CH₃ | 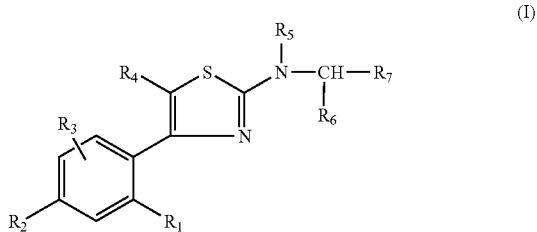 | MS(MH⁺) = 483<br>95; [α]$^{20}_D$ = −230° (c = 1.26 CH₂Cl₂) |

The invention claimed is:

1. A method of modulation of the action of corticotropin releasing factor, which comprises administering to a patient in need of such modulation a therapeutically effective amount of a compound of formula (I):

(I)

wherein $R_1$ and $R_2$, which may be identical or different, each independently represent a halogen atom; a hydroxy ($C_1$-$C_5$) alkyl; a ($C_1$-$C_5$)alkyl; an aralkyl in which the aryl portion is ($C_6$-$C_8$) and the alkyl portion is ($C_1$-$C_4$); a ($C_1$-$C_5$)alkoxy; a trifluoromethyl group; a nitro group; a nitrile group; a group —SR in which R represents hydrogen, a ($C_1$-$C_5$)alkyl or an aralkyl in which the aryl portion is ($C_6$-$C_8$) and the alkyl portion is ($C_1$-$C_4$); a group —S—CO—R in which R represents a ($C_1$-$C_5$)alkyl or an aralkyl radical in which the aryl portion is ($C_6$-$C_8$) and the alkyl portion is ($C_1$-$C_4$); a group —COORa in which Ra represents hydrogen or a ($C_1$-$C_5$)alkyl; a group —CONRaRb with Ra and Rb as defined above for Ra; a group —NRaRb with Ra and Rb as defined above for Ra; a group —CONRcRd or —NRcRd in which Rc and Rd constitute, with the nitrogen atom to which they are attached, a 5- to 7-membered heterocycle; or a group —NHCO—NRaRb with Ra and Rb as defined above for Ra;

$R_3$ represents hydrogen or is as defined above for $R_1$ and $R_2$;

or alternatively $R_2$ constitutes with $R_3$, when the latter substitutes the phenyl in position 5, a group —X—CH₂—X— in which X independently represents a CH₂ or an oxygen or sulphur atom;

$R_4$ represents hydrogen, a ($C_1$-$C_5$)alkyl; a hydroxymethyl group; a formyl group; a halogen atom; or a ($C_3$-$C_5$) cycloalkyl group;

$R_5$ represents an alkynyl of 3 to 6 carbon atoms;

$R_6$ represents a ($C_1$-$C_6$)alkyl; a ($C_1$-$C_6$)alkoxy($C_1$-$C_3$) alkyl; a ($C_3$-$C_5$)cycloalkyl; a ($C_3$-$C_6$)cycloalkyl($C_1$-$C_6$) alkyl; a ($C_1$-$C_6$)alkylthio($C_1$-$C_3$)alkyl; a ($C_1$-$C_6$)alkyl-sulphoxy($C_1$-$C_3$)alkyl; or a ($C_1$-$C_6$)alkylsulphodioxy ($C_1$-$C_3$)alkyl; and $R_7$ represents a phenyl which is unsubstituted, mono-, di- or trisubstituted in position 3, 4 or 5 with a halogen, with a ($C_1$-$C_5$)alkyl, with an —O—CH₂—O— group on two neighbouring carbon atoms of the phenyl, with a —CF₃, —NO₂ or —CN, with a group —COOR₈ or —CONR₈R₉ or with a group —CH₂OR₈ in which R₈ and R₉ represent a ($C_1$-$C_3$)alkyl, OR₁₀ in which R₁₀ represents a ($C_1$-$C_5$)alkyl; or alternatively R₇ represents a pyridyl, thiophene, pyrazolyl, imidazolyl, ($C_3$-$C_5$)cycloalkyl or ($C_3$-$C_6$)cycloalkyl($C_1$-$C_6$)alkyl group; or an acid or base addition salt thereof.

2. The method according to claim 1 wherein said modulation treats a disease chosen from depression, anxiety, panic, obsessive compulsive disorders, mood disorders, post-traumatic stress, behavioral disorders, aggressiveness, anorexia, bulimia, hyperglycemia, premature labor, at-risk pregnancy, retarded growth, sleeping disorders and epilepsy.

3. A method of modulation of the action of corticotropin releasing factor, which comprises administering to a patient in need of such modulation a therapeutically effective amount of a compound of formula (I.2):

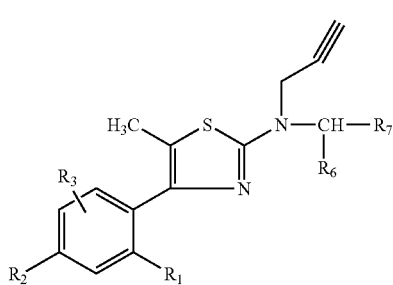

(I.2)

wherein
$R_1$ and $R_2$, which may be identical or different, each independently represent a halogen atom; a $(C_1-C_5)$alkyl; or a $(C_1-C_5)$alkoxy;

$R_3$ represents hydrogen or is as defined above for $R_1$ and $R_2$;

$R_6$ represents a $(C_1-C_6)$alkyl; a $(C_1-C_6)$alkoxy$(C_1-C_3)$ alkyl; a $(C_3-C_5)$cycloalkyl; or a $(C_3-C_6)$cycloalkyl$(C_1-C_6)$alkyl; and $R_7$ represents a phenyl which is unsubstituted or mono- or disubstituted in position 3 or 4 with a halogen, a $(C_1-C_5)$ alkyl group, a group —CH$_2$OR$_8$ in which R$_8$ represents a $(C_1-C_3)$alkyl or with an —O—CH$_2$—O— group in position 3, 4; or alternatively $R_7$ represents a $(C_3-C_5)$ cycloalkyl group; or an acid or base addition salt thereof.

4. The method according to claim 3 wherein said modulation treats a disease chosen from depression, anxiety, panic, obsessive compulsive disorders, mood disorders, post-traumatic stress, behavioral disorders, aggressiveness, anorexia, bulimia, hyperglycemia, premature labor, at-risk pregnancy, retarded growth, sleeping disorders and epilepsy.

5. A method of modulation of the action of corticotropin releasing factor, which comprises administering to a patient in need of such modulation a therapeutically effective amount of a compound selected from the group consisting of:

[4-(2-chloro-4-methoxy-5-methylphenyl)-5-methylthiazol-2-yl][(1R)-(1-(3-fluoro-4-methylphenyl)-2-methoxyethyl)]prop-2-ynylamine;

[4-(2-chloro-4-methoxy-5-methylphenyl)-5-methylthiazol-2-yl][(1S)-(1-phenylbutyl)]prop-2-ynylamine;

[4-(2-chloro-4-methoxy-5-methylphenyl)-5-methylthiazol-2-yl][(1S)-(2-cyclopropyl-1-phenylethyl)]prop-2-ynylamine;

[4-(2-chloro-4-methoxyphenyl)-5-methylthiazol-2-yl] [(1S)-(2-cyclopropyl-1-phenylethyl)]prop-2-ynylamine;

[4-(2-chloro-4-methoxy-5-methylphenyl)-5-methylthiazol-2-yl][(1S)-(2-cyclopropyl-1-(4-fluorophenyl) ethyl)]prop-2-ynylamine;

[4-(2-chloro-4-methoxy-5-methylphenyl)-5-methylthiazol-2-yl][(1S)-(1-phenylpentyl)]prop-2-ynylamine;

[4-(2-chloro-4-methoxy-5-methylphenyl)-5-methylthiazol-2-yl][(1R)-(2-methoxy-1-(4-methoxymethylphenyl)ethyl)]prop-2-ynylamine;

[4-(2-chloro-4-methoxy-5-methylphenyl)-5-methylthiazol-2-yl][(1S)-(1-(4-methoxymethylphenyl)pentyl)] prop-2-ynylamine;

[4-(2-chloro-4-methoxy-5-methylphenyl)-5-methylthiazol-2-yl][(1S)-(1-(4-fluorophenyl)pentyl)]prop-2-ynylamine;

[4-(2-chloro-4-methoxy-5-methylphenyl)-5-methylthiazol-2-yl][(1S)-(cyclopropylphenylmethyl)]prop-2-ynylamine;

[4-(2-chloro-4-methoxy-5-methylphenyl)-5-methylthiazol-2-yl][(1S)-(1-(3-fluoro-4-methylphenyl)pentyl)] prop-2-ynylamine;

[4-(2-chloro-4-methoxy-5-methylphenyl)-5-methylthiazol-2-yl][(1S)-(2-cyclopropyl-1-(3-fluoro-4-methylphenyl)ethyl)]prop-2-ynylamine;

[4-(2-chloro-4-methoxy-5-methylphenyl)-5-methylthiazol-2-yl][(1S)-(1-(4-fluorophenyl)butyl)]prop-2-ynylamine;

[4-(2-chloro-4-methoxy-5-methylphenyl)-5-methylthiazol-2-yl][(1S)-(1-(3-fluoro-4-methoxymethylphenyl) butyl)]prop-2-ynylamine;

[4-(2-chloro-4-methoxy-5-methylphenyl)-5-methylthiazol-2-yl][(1S)-(2-cyclopropyl-1-(4-chlorophenyl) ethyl)]prop-2-ynylamine;

[4-(2-chloro-4-methoxy-5-methylphenyl)-5-methylthiazol-2-yl][(1S)-(2-cyclopropyl-1-(4-methylphenyl) ethyl)]prop-2-ynylamine;

[4-(2-chloro-4-methoxy-5-methylphenyl)-5-methylthiazol-2-yl][(1S)-(2-cyclobutyl-1-(4-fluorophenyl) ethyl)]prop-2-ynylamine;

[4-(2-chloro-4-methoxy-5-methylphenyl)-5-methylthiazol-2-yl][(1S)-(2-cyclopropyl-1-(4-bromophenyl) ethyl)]prop-2-ynylamine;

[4-(2-chloro-4-methoxy-5-methylphenyl)-5-methylthiazol-2-yl][(1S)-(2-cyclopropyl-1-(3,4-methylenedioxyphenyl)ethyl)]prop-2-ynylamine;

[4-(2-chloro-4-methoxyphenyl)-5-methylthiazol-2-yl] [(1S)-(2-cyclopropyl-1-(3-fluoro-4-methylphenyl) ethyl)]prop-2-ynylamine;

[4-(2,4-dimethoxy-5-methylphenyl)-5-methylthiazol-2-yl][(1S)-(2-cyclopropyl-1-(3-fluoro-4-methylphenyl) ethyl)]prop-2-ynylamine;

[4-(4-methoxy-2,5-dimethylphenyl)-5-methylthiazol-2-yl][(1S)-(2-cyclopropyl-1-(3-fluoro-4-methylphenyl) ethyl)]prop-2-ynylamine; and

[4-(2-chloro-4-methoxy-5-methylphenyl)-5-methylthiazol-2-yl][(1S)-(1-(3,4-methylenedioxyphenyl)butyl)] prop-2-ynylamine; or an acid or base addition salt thereof.

6. The method according to claim 5 wherein said modulation treats a disease chosen from depression, anxiety, panic, obsessive compulsive disorders, mood disorders, post-traumatic stress, behavioral disorders, aggressiveness, anorexia, bulimia, hyperglycemia, premature labor, at-risk pregnancy, retarded growth, sleeping disorders and epilepsy.

* * * * *